United States Patent [19]

Pak et al.

[11] Patent Number: 5,228,445
[45] Date of Patent: Jul. 20, 1993

[54] DEMONSTRATION BY IN VIVO MEASUREMENT OF REFLECTION ULTRASOUND ANALYSIS OF IMPROVED BONE QUALITY FOLLOWING SLOW-RELEASE FLUORIDE TREATMENT IN OSTEOPOROSIS PATIENTS

[75] Inventors: Charles Y. C. Pak, Dallas; Peter Antich, Richardson, both of Tex.

[73] Assignee: Board of Regents, The University of Texas System, Austin, Tex.

[21] Appl. No.: 813,383

[22] Filed: Dec. 26, 1991

Related U.S. Application Data

[63] Continuation-in-part of Ser. No. 717,025, Jun. 18, 1991, and a continuation-in-part of Ser. No. 539,993, Jun. 18, 1990, abandoned.

[51] Int. Cl.$^5$ .................................................. A61B 8/00
[52] U.S. Cl. ............................ 128/660.01; 128/661.03
[58] Field of Search ................. 128/660.01, 660.03, 128/660.06, 661.03

[56] References Cited

U.S. PATENT DOCUMENTS

| | | |
|---|---|---|
| 4,094,304 | 6/1978 | Wright, Jr. . |
| 4,098,129 | 7/1978 | Deblaere et al. . |
| 4,361,154 | 11/1982 | Pratt, Jr. . |
| 4,364,273 | 12/1982 | Redding . |
| 4,421,119 | 12/1983 | Pratt, Jr. . |
| 4,437,468 | 3/1984 | Sorenson et al. . |
| 4,457,311 | 7/1984 | Sorenson et al. . |
| 4,458,689 | 7/1984 | Sorenson et al. . |
| 4,476,873 | 10/1984 | Sorenson et al. . |
| 4,682,497 | 7/1987 | Sasaki . |
| 4,726,952 | 2/1988 | Walsdorf . |
| 4,851,221 | 7/1989 | Pak et al. . |
| 4,904,478 | 2/1990 | Walsdorf et al. . |
| 5,038,787 | 8/1991 | Antich et al. . |

OTHER PUBLICATIONS

Antich et al., *J. Bone and Mineral Research*, 6:417–426 (1991).
Antich et al., "A Novel Method for Characterizing Bone Strength at the Trabecular Level", Abstract 999, *Journal of Bone and Mineral Research*, 4 (Supplement): S367 (1989).
Whiting, "Ultrasonic Critical Angle Reflection Goniometer for In Vivo Bone", *Ultrasound in Medicine*, 1629–1643 (Plenum: New York, 1977).
Mayer, *Journal of Accoustical Society of America*, 32:1213 (1960).
Mayer, *Journal of Applied Physics*, 34:909–911, (1963).
Lees, *Ultrasonics*, 213–215 (Sep. 1975).
Fountain, *Journal of Acoustical Society of America*, 42:242–247 (1967).
Mayer, *Ultrasonics*, 62–68 (Apr.–Jun., 1965).
Couchman et al., *Ultrasonics*, 69–71 (Mar., 1974).

(List continued on next page.)

Primary Examiner—Francis Jaworski
Attorney, Agent, or Firm—Arnold, White and Durkee

[57] ABSTRACT

The invention involves a treatment process for improving the intrinsic quality of bone in osteoporotic patients. This can reduce the frequency of spinal fractures by inducing formation of bone which is mechanically stronger than that which it replaces. The process preferably comprises: administering an enteral form of sodium fluoride to maintain an individual's serum fluoride level from about 100 to about 200 ng/ml with a circadian fluctuation of less than about 75 ng/ml, and dietarily supplementing said individual with absorbable calcium (preferably calcium citrate). In one embodiment, sodium fluoride administration is interrupted temporarily (for about 30 to about 60 days in a 13 or 14 month cycle) to prevent loss of fluoride effectiveness and avert impaired mineralization of bone. Calcium is preferably maintained by an enteral dose of about 400 mg calcium twice daily. A vitamin D preparation may also be administered to the individual to further enhance bone strengthening. As a method for assessing response, periodic noninvasive in vivo measurements of intrinsic bone quality are made by reflection ultrasound, and the treatment regimen is maintained, altered or discontinued based on clinical assessment of the results. In this way, clinical response to the treatment is evaluated to guide its continued application.

5 Claims, 12 Drawing Sheets

OTHER PUBLICATIONS

Rollins, *Journal of Acoustical Society of America*, 44:431–434 (Feb., 1968).
Lees et al., *J. Biomechanics*, 5:557–566, (1972).
Weston-Bartholomew, *Ultrasonics*, 132–135, (May 1973).
"Ultrasonic Bone Scanning Device", *Biologue*, p. 6 (1987–1988).
Currey, *Clinical Orthopedics and Related Research*, 210–231 (Nov.–Dec. 1970).
Abendschein, *Clinical Orthopedics and Related Research*, 294–301 (Mar.–Apr. 1970).
Greenfield, *Utrasound*, 115:163–166 (1975).
Greenfield, *Radiation Physics*, 138:701–710 (1981).
Craven, *Investigative Radiology*, 8:72–77 (1973).
Lees, *Sonic Properties of Mineralized Tissues, Tissue Characterization with Ultrasound*, Chapter 9, pp. 207–226 (1986).
Ashman et al., "Elastic Properties of Cancellous Bone: Measurement By An Ultrasonic Technique", 1986 SEM Spring Conference on Experimental Mechanics.
Ashman et al., *J. Biomechanics*, 17:349–361 (1984).
"Ultrasound Scanner Proving Effectiveness of Osteoporosis Drug", *Center Times*, p. 3 (May 1991).
Antich et al., "Measurement of Intrinsic Bone Strength In Vivo by Reflection Ultrasound: Correction of Impaired Strength With Slow Release Sodium Fluoride in Calcium Citrate", (in press).
Pak et al., "Fracture Incidence-Bond Density Relationship: A Reference for Interpreting the Effect of Slow-Release Sodium Flouride Plus Calcium Citrate Treatment on Spinal Fracture Rate," (in press).
Riggs et al., *N. Eng J. Med*, 322:802–809 (1990).
Pak et al., *J Bone Min Res*, 5(Supp 1):S149–S155 (1990).
Zerwekh et al., (J. Bone Mineral Res. (4) Supplement, p. S367, Abstract 998, (1989).
Pak et al., *JCE & M*, 68(1):150–159 (1989).
Odvina et al., *Metabolism*, 37(3):221–228 (1988).
Holmes et al., *J. Biomed Materials Res*, 21:731–739 (1987).
Eastell et al., *Ob Gyn Clin N Amer*, 14(1):77–88 (1987).
Riggs et al., *N Engl J Med*, 314(26):1676–1686 (1986).
Pak et al., *J Bone Min Res*, 1(6):563–571 (1986).
Riggs et al., *J Clin Invest*, 67:328–335 (1981).
Lindsay, N. *Eng. J. Med.*, 322:845–846 (1990).
Jowsey et al., *Am. J. Med.*, 53:43–49, (Jul. 1972) "Effect of Combined Therapy with Sodium Fluoride, Vitabmin D and Calcium in Osteoporosis".
Zerwekh et al. manuscript, currently in press, *J. Bone Min. Res.* (Mar. 1991).
Storm et al., *N. Eng. J. of Med.*, 322:1265–1271 (May 1990), "Effect of Intermittent Cyclical Etidronate Therapy on Bone Mass and Fracture Rate in Women with Postmenopausal Osteoporosis."
Watts et al., *New England J. Med.*, 323:73–79, (Jul. 1990), "Intermittent Cyclical Etidronate Treatment of Postmenopausal Osteoporosis."
Sakhaee et al., *Bone and Mineral*, 14:131–136, (1991) "Fluoride bioavailability from immediate-release sodium fluoride with calcium carbonate compared with slow-release sodium fluoride with calcium citrate."
Antich et al. *J. Bone Min. Res.* 6:417–426 (Mar. 1991) "Measurement of Mechanical Propereties of Bone Material *In Vitro* by Ultrasound Reflection: Methodology and Comparison with Ultrasound Transmission."
Wells PNT et al., Churchill Livingstone, N.Y. (1977) "Ultrasonics in Clinical Diagnosis."

DEMONSTRATION BY IN VIVO MEASUREMENT OF REFLECTION ULTRASOUND ANALYSIS OF IMPROVED BONE QUALITY FOLLOWING SLOW-RELEASE FLUORIDE TREATMENT IN OSTEOPOROSIS PATIENTS

This is a continuation-in-part of U.S. patent application Ser. No. 07/539,993, filed Jun. 18, 1990 and now abandoned. Research leading to development of the present invention was supported in part by grants RO1-AR16061 and MO1-RR00633 from the National Institutes of Health, Department of Health and Human Services, United States of America, and from Vitel, Inc.

BACKGROUND OF THE INVENTION

This is a continuation-in-part of Ser. No. 07/717,025 filed Jun. 18, 1991 and of 07/539,993 filed Jun. 18, 1990 and now abandoned, both of which are incorporated by reference herein.

Osteoporosis is a chronic disease of bone in which bones break with minimum trauma. Thus, patients suffering from this condition may sustain fractures of backbone (vertebra) or of the hip, while lifting a grandchild or following a minor fall, incidents which normally would not cause fractures.

The increased risk of fractures in osteoporotic persons has been traditionally ascribed to the loss of bone mass which thereby weakens bone. The loss of bone in osteoporosis has been shown by radiolucency ("lighter" image) on x-ray of bone, reduced amount of trabeculae (microscopic units of bone) on bone biopsy, as well as by bone density measurements. Using recently developed densitometers, bone density in the spine and the hip has been shown to be typically reduced by 30-50% in osteoporotic individuals (Riggs et al., *J. Clin. Invest.* Vol 67:328-335, 1981).

Thus, bone density measurements have been used to assess the severity of osteoporosis and the risk of developing fractures. Such measurements have led to the calculation of "fracture threshold," the level of bone density below which the risk of fractures is increased progressively (Odvina et al. *Metabolism*, Vol 37:221-228, 1988).

According to the same principles, it has been traditionally believed that, in order to prevent further fractures in patients with established osteoporosis, treatments must increase bone mass until the bone density exceeds fracture threshold (Eastell and Riggs, *Obst. Gyn. Clin. N. Am.*, Vol 14: 77-88, 1987).

Fluoride is a drug which can clearly stimulate new bone formation and thus is capable of restoring lost bone in the spine (Pak et al., *J. Clin. Endo. Metab.*, Vol 68:150-159, 1989). However, in a recent trial which included a placebo group, sodium fluoride in a plain immediate-release form at a high dosage of 75 mg/day with calcium carbonate over 4 years failed to reduce spinal fractures, even though bone density increased by 35% (Riggs et al., *New Engl. J. Med.*, Vol 322:802-809, 1990). The results suggested the possibility that bone quality may have deteriorated from formation of abnormal bone during this form of treatment, offsetting the benefits of increased bone mass.

Thus, the tendency of developing fractures of bone is not only determined by bone density but also by bone quality. This assertion could explain the lack of fractures in some individuals who have low bone density (below fracture threshold). Conversely, recurrent fractures of bone in osteoporotic patients may be prevented by treatments which improve the quality of bone. This approach is attractive because prior art methods of making more bone are hazardous, too slow or associated with abnormal bone formation.

In two prior patents including the present inventor (U.S. Pat. No. 4,726,952 and U.S. Pat. No. 4,888,182, both incorporated by reference herein), treatment of osteoporotic patients with sodium fluoride in a slow release tablet formulation was shown to keep blood fluoride within safe and effective levels ("therapeutic window") and provide safety of usage (Pak et al., *J. Bone Miner. Res.*, Vol 1:563-571, 1986). Unlike the immediate release sodium fluoride used by others, the slow release sodium fluoride caused minor and infrequent undesired side effects. When used with calcium citrate, spinal bone mass rose and the rate of spinal fractures decreased (as compared to the rate before treatment) (Pak et al., *J. Clin. Endo. Metab.*, Vol 68:150-159, 1989). The reduction in fracture rate was ascribed to the rise in bone mass. No consideration or mention was made of the change in quality of bone by this treatment in either patent or publications. Calcium citrate dietary supplementation by itself has been shown by the present inventor to inhibit development of osteoporosis (U.S. Pat. No. 4,772,467, incorporated by reference herein), but it was not envisioned to make more bone or improve bone quality.

Subsequently, continuing experience with slow release sodium fluoride treatment of osteoporosis indicated that if this treatment was concomitant with calcium citrate supplementation the quality of bone was improved and spinal fractures thereby inhibited, even when the rise in bone mass was modest and the bone density remained below the fracture threshold. This finding is an important basis of this patent application.

Similarly, the recognition that not all patients with osteoporosis respond favorably to treatment with sodium fluoride and calcium citrate is important because it implies that bone quality must be monitored during treatment. Heretofore, such monitoring would have required periodic bone biopsies (Antich et al., *J. Bone Miner. Res.*, 6(4):417-426 (1991); Zerwekh et al., *J. Bone Miner. Res.*, 6(3):239-244 (1991)), but the present invention discloses a method for non-invasive, in vivo monitoring of bone quality.

SUMMARY OF THE INVENTION

The invention involves firstly a treatment process for improving the quality and increasing the mechanical strength, structural integrity, and resistance to fracture of bone in osteoporotic patients, and secondly a method for assessing therapeutic response and the need for further treatment. The treatment can reduce the frequency of spinal fractures without necessarily increasing bone density by inducing formation of bone which is mechanically stronger than that which it replaces. The method can also be used to assess the degree of healing of a fracture.

The treatment process comprises: maintaining an individual's serum fluoride level from about 100 to about 200 ng/ml (therapeutic window) with a circadian fluctuation of less than about 75 ng/ml, and dietarily supplementing said individual with absorbable calcium.

The calcium supplement is preferably a highly absorbable form such as calcium citrate, although other calcium salts, including calcium carbonate, may be used if they can be shown to be efficiently absorbed in a given patient. The fluoride level is maintained by an oral administration of sodium fluoride in a slow release form. A preferred sodium fluoride dosage is 25 mg twice per day. A slow-release form of sodium fluoride is preferably one comprising carnauba wax and talc, although other slow-release forms may be used if suitable to maintain the fluoride levels within the prescribed therapeutic window and circadian fluctuation. Sodium fluoride administration is preferably enteral. The sodium fluoride administration, in one embodiment, is interrupted temporarily (for about 30 to about 60 days) to prevent loss of effectiveness of fluoride and avert impaired mineralization of bone.

Calcium citrate is the most preferred highly absorbable calcium administered enterally by tablets or dietary supplementation. The calcium is preferably at a dose of about 400 mg calcium twice per day, and a vitamin D preparation may also be administered to the individual to further enhance intestinal calcium absorption.

A preferred process comprises intermittent treatment with slow release sodium fluoride (25 mg twice daily for the first 12 months in each 13-14 month cycle) and continuous calcium citrate dietary supplementation (400 mg calcium twice daily).

The method for assessing therapeutic response and degree of fracture healing is an ultrasound analysis of bone in vivo. A preferred method comprises periodic in vivo monitoring of cancellous and cortical bone quality by measurement of reflection ultrasound velocities in the ulna or other suitably accessible bone or across an accessible fracture site in a bone. The use of this method to measure bone quality as a determinate of bone strength has been shown by one of the inventors (U.S. Pat. No. 5,038,787). Decisions to continue, modify, or discontinue therapy are made by comparing measured changes in reflection ultrasound velocities over time with clinically acceptable objectives.

DESCRIPTION OF THE PREFERRED EMBODIMENTS

Figure 1:
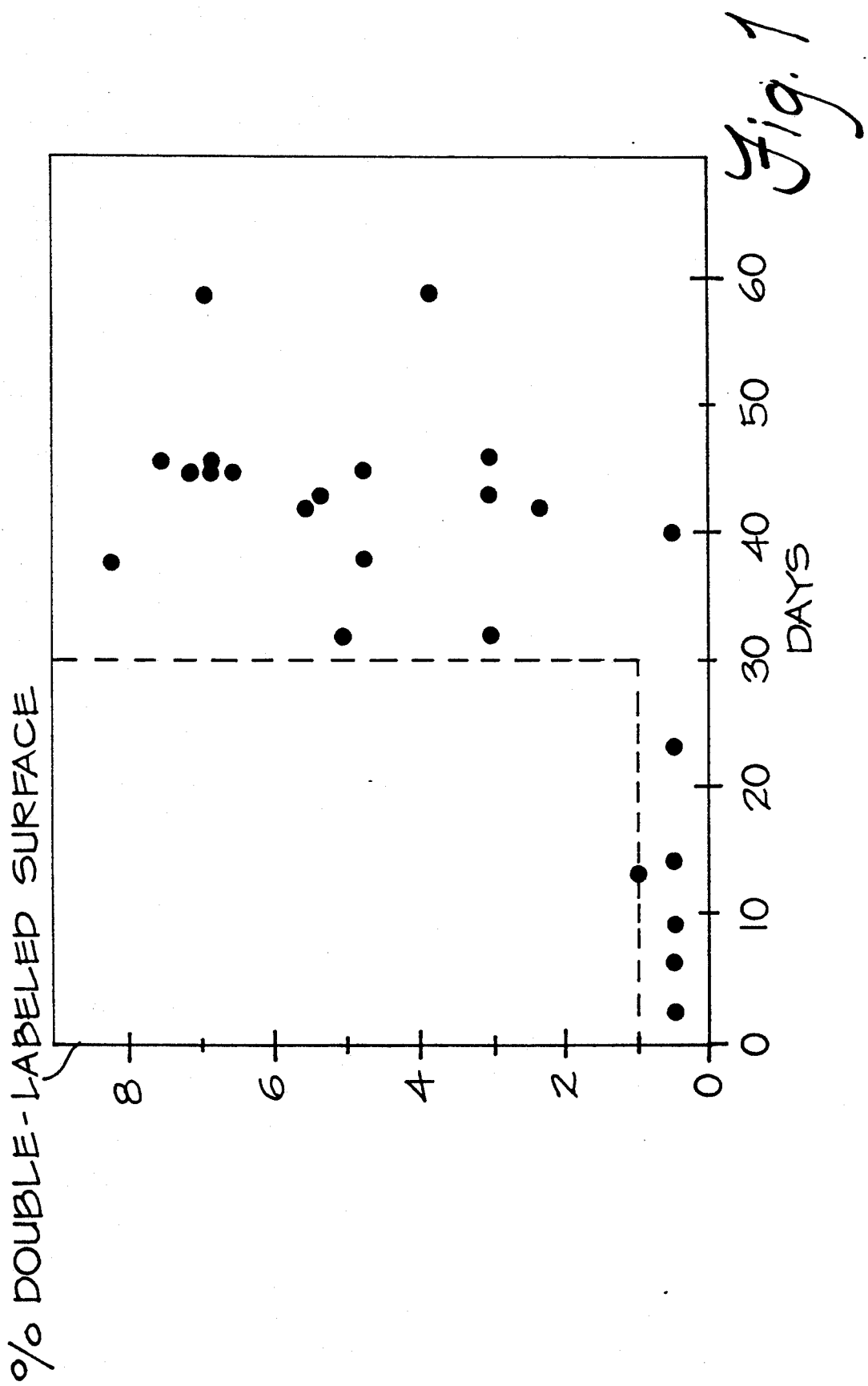
FIG. 1 shows tetracycline labelling of bone from subjects after a withdrawal from fluoride of less than 30 days (6 subjects) or 30-60 days (18 subjects) in patients who received treatment with slow release sodium fluoride for two years.

A detailed description of the treatment regimen constituting the invention, and the evidence that it improves bone quality are as follows. The preferred treatment is intermittent administration of slow release sodium fluoride and continuous calcium citrate supplementation. Typically, slow release sodium fluoride (25 mg), is given together with calcium citrate (400 mg calcium) on an empty stomach twice per day before breakfast and at bedtime, during the first 12 months of each 13 or 14 mo. cycle, with the cycle being repeated. During the last 1 or 2 months of each cycle, calcium citrate alone is provided while fluoride treatment is withheld (Pak et al., *J. Bone Miner. Res.*, vol 5:S149-S155, 1990). By using sodium fluoride in a slow release formulation (as embodied in U.S. Pat. No. 4,726,952 and U.S. Pat. No. 4,888,182), the serum fluoride level is kept within the therapeutic window (95-190 ng/ml) without a wide circadian fluctuation (Pak et al., *J. Bone Miner. Res.*, Vol 1:563-561, 1986).

The purpose of withdrawing fluoride treatment for 1-2 months is to avert loss of effectiveness on stimulation of bone formation which may occur with continuous long-term treatment (Example 1). Calcium citrate, embodied in U.S. Pat. No. 4,772,467 and U.S. Pat. No. 4,814,177 (incorporated by reference herein), is given to provide an optimum amount of calcium to be absorbed from the intestinal tract, so as to permit adequate mineralization of bone which is stimulated to form by fluoride.

The following results indicate that this invention succeeds in making bone that is stronger and of improved quality. First, bone biopsy specimens taken from patients who received approximately two years of treatment showed normally mineralized bone by light and electron microscopy (Example 2). Second, bone biopsy samples were examined by a new reflection ultrasound technique which measures strength of bone. This study showed that bone samples following treatment were improved in quality compared to samples before treatment (Example 3). Third, the measurement of reflection ultrasound velocity of ulvar bone in vivo confirmed the in vitro finding that the treatment with slow release sodium fluoride and calcium citrate improves bone quality (Example 4). Fourth, the spinal fracture number during slow release sodium fluoride treatment was significantly less than that of untreated osteoporotic patients at same level of bone density (Example 5). Fifth, the cancellous ultrasound velocity was inversely correlated with vertebral fracture number (Example 6).

The following Examples are included to describe the best mode of the present invention but are not intended to limit the scope of the invention unless otherwise specified in the appended claims.

EXAMPLE 1

Restoration of Loss of Effectiveness of Fluoride Treatment by A Temporary Fluoride Withdrawal Newly-formed areas of bone pick up tetracycline, which on microscopic examination of biopsied bone appears as "lines" of distinct color. When two courses of tetracycline are given orally to patients separated by a fixed period (for example, 10 days), bone biopsy will normally show two distinct lines. The distance between the two lines represents bone newly formed during that interval.

Transiliac crest bone biopsy was performed and the specimens examined histomorphometrically in 24 osteoporotic patients after they received slow-release sodium fluoride treatment for about two years. The tetracycline labelling of bone was initiated at various times after slow-release sodium fluoride withdrawal. In 6 patients, in whom the duration of fluoride withdrawal before tetracycline labelling was less than 30 days, the percent of surface showing double labelling with tetracycline was low ($<1\%$), a finding indicating that the fluoride-stimulation of osteoblasts was attenuated and/or that there was a defect in mineralization (FIG. 1). However, in remaining patients in whom the duration of fluoride withdrawal before tetracycline labelling was greater than 30 days, the percent of double-labelled surface was substantially higher, and significantly greater than the value obtained before treatment. These results indicated that withdrawal of fluoride therapy for at least 30 days could avert fluoride tachyphylaxis and assure adequate formation and mineralization.

EXAMPLE 2

Normal Bone Mineralization by Light and Electron Microscopy

Bone biopsy (from iliac crest) was obtained after approximately 2 years of treatment with intermittent slow release sodium fluoride and continuous calcium citrate in 26 patients with osteoporosis.

Figure 2:
FIG. 2 shows a microscopic example of bone with orderly "layering".

Every bone sample, examined by light microscopy under polarized light, showed entirely normal lamellar bone. An example of lamellar bone with orderly "layering" is shown in FIG. 2. No mosaic bone with disorderly layering, reported to occur in fluorosis, was seen.

Figure 3:
FIG. 3 shows backscattered electron image analysis of a subject's newly formed bone.

Each bone sample was also examined by backscattered electron image, a new technique designed to examine adequacy of mineralization in bone (Holmes et al., *J. Biomed. Nat. Res.*, Vol 21:731-739, 1987). In this technique, the image formed by backscatter of electrons is proportional to the atomic number of material scanned. Thus, on a scanning electron micrograph, areas of low density (newly formed bone) appear darker than old bone. Every specimen showed normal mineralization of newly formed bone. An example is shown in FIG. 3. An orderly layering of bone can also be visualized in darker newly formed bone.

EXAMPLE 3

Improved Material Strength of Biopsied Bone by Reflection Ultrasound

A pair of bone biopsies (iliac crest) obtained before and after approximately 2 years of treatment with slow release sodium fluoride with calcium citrate from each of 16 osteoporotic patients was examined by a newly developed reflection ultrasound technique (Antich et al. *J. Bone Min. Res.* 6:417-426 (1991); Zerwekh et al. *J. Bone Min. Res.*, 6:239-244 (1991).

This technique measures velocity of ultrasound reflected from bone trabeculae (microscopic spicules of bone). It is obtained at the critical angle when all ultrasound is reflected and none transmitted. Using a high frequency ultrasound, a small area of bone can be scanned, corresponding to 1-2 units of trabeculae. The velocity corresponds to elasticity which in turn determines strength. Thus, the reflection ultrasound velocity provides a measure of bone strength at the trabecular (material) level. Bone strength, structural integrity, and resistance to fracture vary directly in proportion to the reflection ultrasound velocity, which has been shown to correlate directly with the mechanical property of bone.

The reflection ultrasound technique differs from the transmission ultrasound method. The latter measures velocity transmitted across a piece of bone; thus, it is also a function of whole bone mass and gives a measure of structural property. Replacement of bone by soft tissue or fluid, as in the early stages of fracture healing, would reduce the velocity measured across a fracture site.

For the group, the reflection ultrasound velocity of cancellous bone from bone biopsy specimens increased significantly from $3336 \pm 33$ m/sec before treatment to $3496 \pm 26$ m/sec ($p < 0.0001$) following treatment (Zerwekh et al. *J. Bone Min. Res.*, 6:239-244 (1991). In 80% of patients, the ultrasound velocity was higher before treatment than after treatment. The results indicated that treatment with slow release sodium fluoride and calcium citrate increases the strength of cancellous bone at the level of trabeculae.

In 15 osteoporotic patients, transiliac crest bone biopsies obtained before and after 2 years of slow release sodium fluoride (SRNaF) and calcium citrate treatment were examined in cortical bone (Zerwekh et al. *Bone and Mineral*, accepted 1991). The skeletal fluoride content and the mean atomic number (density or $Z^*$) increased significantly with treatment (Table 1).

TABLE 1

Reflection ultrasound velocity, Z*, and skeletal fluoride content in pre- and post-SRNaF biopsies for cortical bone in 15 osteoporotic patients.

| Cortical | Pre | Post | |
|---|---|---|---|
| Velocity (m/sec) | 4000 ± 227[a] | 4013 ± 240 | |
| Z* | 9.261 ± 0.311 | 9.457 ± 0.223 | (P = 0.031) |
| Skeletal F (% ash weight) | 0.095 ± 0.045 | 0.163 ± 0.080 | (P = 0.0017) |

[a]Values expressed as mean ± SD.
The reflection ultrasound velocity in cortical bone did not decline. The results suggest that this treatment does not adversely effect cortical bone, unlike high fluoride dose regimens (Riggs et al. New Engl. J. Med., Vol 322:802-809 (1990)).

EXAMPLE 4

Measurement of Intrinsic Bone Quality in vivo By Reflection Ultrasound Measurements On the Ulnar Read and Shaft The intrinsic (material) quality of cancellous and cortical bone was evaluated in vivo from the measurement of reflection ultrasound velocities in the ulna. In cancellous bone, the reflection ultrasound velocity was inversely correlated with age in normal women ($r = -0.48$, $p = 0.001$), with a significantly lower mean value in 32 normal postmenopausal women than in 14 premenopausal women (3124 m/sec vs 3341 m/sec, $p < 0.0001$). In 32 untreated osteoporotic women the cancellous bone velocity was significantly lower than in normal subjects (2902 m/sec vs 3197 gm/sec, $p < 0.0001$). Most of the values for reflection ultrasound velocity in untreated osteoporotic women were low or low normal (See Example 6).

Following treatment with slow-release sodium fluoride plus calcium citrate (mean 2.4 years in 33 osteoporotic patients with no fracture during treatment), the cancellous bone velocity was within normal limits in most patients; the mean velocity was significantly higher than in untreated osteoporotic women (3082 m/sec vs 2902 m/sec, $p = 0.0002$), but was not significantly different from normal postmenopausal women. Smaller but qualitatively similar changes were found in cortical bone velocity.

The cancellous ultrasound velocity was measured again approximately 9 months later in 9 untreated patients and 20 treated patients. It rose significantly from 3037 to 3167 m/sec ($p = 0.017$) in patients treated for short-term (12-30 months at first measurement), but not in untreated patients or those treated for more than 30 months.

Thus, the material quality of cancellous bone decreases with normal aging, and is reduced further by the osteoporotic process. This reduced quality may be corrected by treatment with slow-release sodium fluoride plus calcium citrate. Efficacy of the treatment can be assessed by a method for reflection ultrasound analysis of the ulna in vivo. This method provides an estimate of intrinsic quality of bone which is related to its modulus of elasticity (resistance to deformation), the latter obtainable from density and reflection ultrasound velocity measurements (Antich et al., *J. Bone Min. Res.*, 6:417-26 (1991)). The method provides direct and separate measurements of cancellous and cortical bone quality from analysis of reflection ultrasound velocities in the ulnar head and shaft respectively.

Materials and Methods

Participating in the study were 120 white women, comprised of 46 normal subjects and 74 patients with osteoporosis. Among normal women, 14 were premenopausal and 32 were postmenopausal. They gave normal menstrual histories with regular premenopausal periods. The postmenopausal women underwent natural menopause; none had surgical oophorectomy. All 46 women were free of pathological skeletal fractures, primary hyperparathyroidism, thyrotoxicosis, hyperadrenocorticism, intestinal malabsorption, chronic diarrheal state, renal stones, alcohol abuse or renal disease (endogenous creatinine clearance less than 0.7 ml/min/kg). They denied taking steroids, anticonvulsants, thyroid hormone, fluoride, diphosphonate, thiazide, calcitonin or vitamin D preparations.

There were 32 women with primary osteoporosis who were not on any specific treatment (untreated osteoporosis). Twenty-seven patients had postmenopausal osteoporosis; 5 were premenopausal women with idiopathic osteoporosis. All had spontaneous spinal fractures. Those with idiopathic osteoporosis gave a normal menstrual history; serum estradiol and gonadotropins were normal. All 32 patients were free of primary hyperparathyroidism, thyrotoxicosis, hyperadrenocorticism, intestinal malabsorption, chronic diarrheal state, renal stones, alcohol abuse, renal disease, or prior therapy with steroids, anticonvulsants, or thyroid hormone. They were not taking estrogen, fluoride, diphosphonate, thiazide, calcitonin or vitamin D preparations.

Besides these untreated women with primary osteoporosis, there were 4 untreated women with steroid-induced osteoporosis. They had taken prednisone at an average dose of 10-20 mg/day for 2-10 years for asthma (in two), polymyalgia rheumatica (in one) and myasthenia gravis (in one). None took diphosphonate, fluoride, calcitonin or estrogen.

Thirty-three patients with primary osteoporosis were treated with slow-release sodium fluoride plus calcium citrate (Pak et al., J. Clin. Endocrin. Metab., 68:150-9 (1989); Pak et al., J. Bone Min. Res., 5:S149-55 (1990)) for 1-6 years (mean 2.4 years); they remained fracture-free during treatment (treated osteoporosis, remission). Two patients had idiopathic osteoporosis, while the remaining women suffered from postmenopausal osteoporosis. The treatment comprised 12-months of treatment with slow-release sodium fluoride (25 mg twice/day), followed by 1 or 2 months of withdrawal in each 13 or 14 month cycle (Pak et al., J. Bone Min. Res., 5:S149-55 (1990)); calcium citrate (400 mg calcium twice/day) was provided continuously. The absence of recurrent spinal fractures was documented by a lack of a decline in vertebral height of more than 15% on repeat spine films (Riggs et al., N. Eng. J. Med., 322:802-9 (1990)) examined with the aid of an electrostatic digitizing board. None of the patients took other fluoride preparations, estrogen, diphosphonate, thiazide, calcitonin or vitamin D preparations. Exclusion criteria were the same as in the untreated osteoporotic group.

Five women with postmenopausal osteoporosis treated with slow-release sodium fluoride and calcium citrate continued to have spinal fractures (treated osteoporosis, relapse).

Procedures

In general, the following tests were performed once for each subject, all on the same day:
bone density of head and shaft (distal third) of nondominant ulna by Hologic QDR-1000; and
reflection ultrasound velocity at the same sites.

The precision of measurement for bone density was 1%. While most patients had all measurements done, the measurement of bone mineral density was not obtained in eight patients, while the cortical and cancellous bone velocity measurements were not obtained in eleven (cortical) and four (cancellous) patients respectively, due to technical difficulties or time constraints.

The cancellous ultrasound velocity measurement was performed a second time 7-11 months later (mean 8.8 months, similar in three groups), in nine untreated osteoporotic women (who were still not receiving fluoride treatment), and 20 treated women in remission (still taking slow-release sodium fluoride and calcium citrate). Among treated patients, the first measurement was performed after less than 30 months of treatment (12-30 months) in nine patients, and after more than 30 months of therapy (30-72 months) in the remaining 11 patients.

Reflection Ultrasound Analysis of Ulna in vivo

The in vivo apparatus determined the critical angle velocity (velocity of reflection ultrasound at the critical angle) in the ulnar head and ulnar shaft, the former yielding cancellous bone velocity and the latter cortical bone velocity. The basic in vivo method was the same as that described for in vitro analysis (Antich et al., *J. Bone Min. Res.*, 6:417-26 (1991)) (U.S. Pat. No. 5,038,787). The system comprised an automated positioning device, a sensor head, and data acquisition electronics.

The positioning device served to locate the center point and to orient the plane of the sensing head relative to the subject's arm. The sensing head consisted of a baseplate with angular transducers about a common axis. Adjustments were provided to allow alignment of the transducers so they lay in the same plane and so the transducer axis intercepted the axis of rotation at the center point. The data acquisition electronics were based on a PC/AT controller. The results were displayed in real time on the operator's screen, as a plot of signal amplitude versus transducer angle. The data were then automatically stored to disk for off-line determination of the critical angle velocity.

The reflection ultrasound velocity was determined separately for cancellous and cortical bone, at the head and distal ⅓ of the ulna respectively. The independent measurement of velocity for two types of bone was possible, since the ultrasound beam is reflected from any surface separating mechanically heterogeneous materials. Signals reflected from soft tissue and cortical bone have slightly different paths than those reflected from the cortical-cancellous bone interface. The two types of signals can therefore be identified by their different times of arrival at the receiver. Furthermore, the value of the critical angle peak of cancellous bone was not altered when thin parallel layers (of soft tissue and cortical bone) were interposed between the cancellous bone and the medium in which the transducers were immersed. These experiments demonstrated that cancellous bone velocity can be measured despite the presence of overlying cortical bone, the precision of individual determinations of velocity being 1.8%. Several measurements were made at each site during the examination, and their mean value was used in the study.

Statistical Methods

An analysis of covariance model was used to assess age-adjusted group effects and age was eliminated as a possible covariate. Therefore, one-way analysis of variance was implemented to compare the mean velocities between the premenopausal, postmenopausal, untreated, remission and relapse groups. Multiple comparisons were performed with two sample t-tests using a Bonferroni adjusted level of significance of 0.005. Ninety-five percent confidence limits for predicting individual outcomes (prediction intervals) were computed for the regression of cancellous bone velocity on age and cancellous bone velocity on ulnar bone density.

Figure 4:
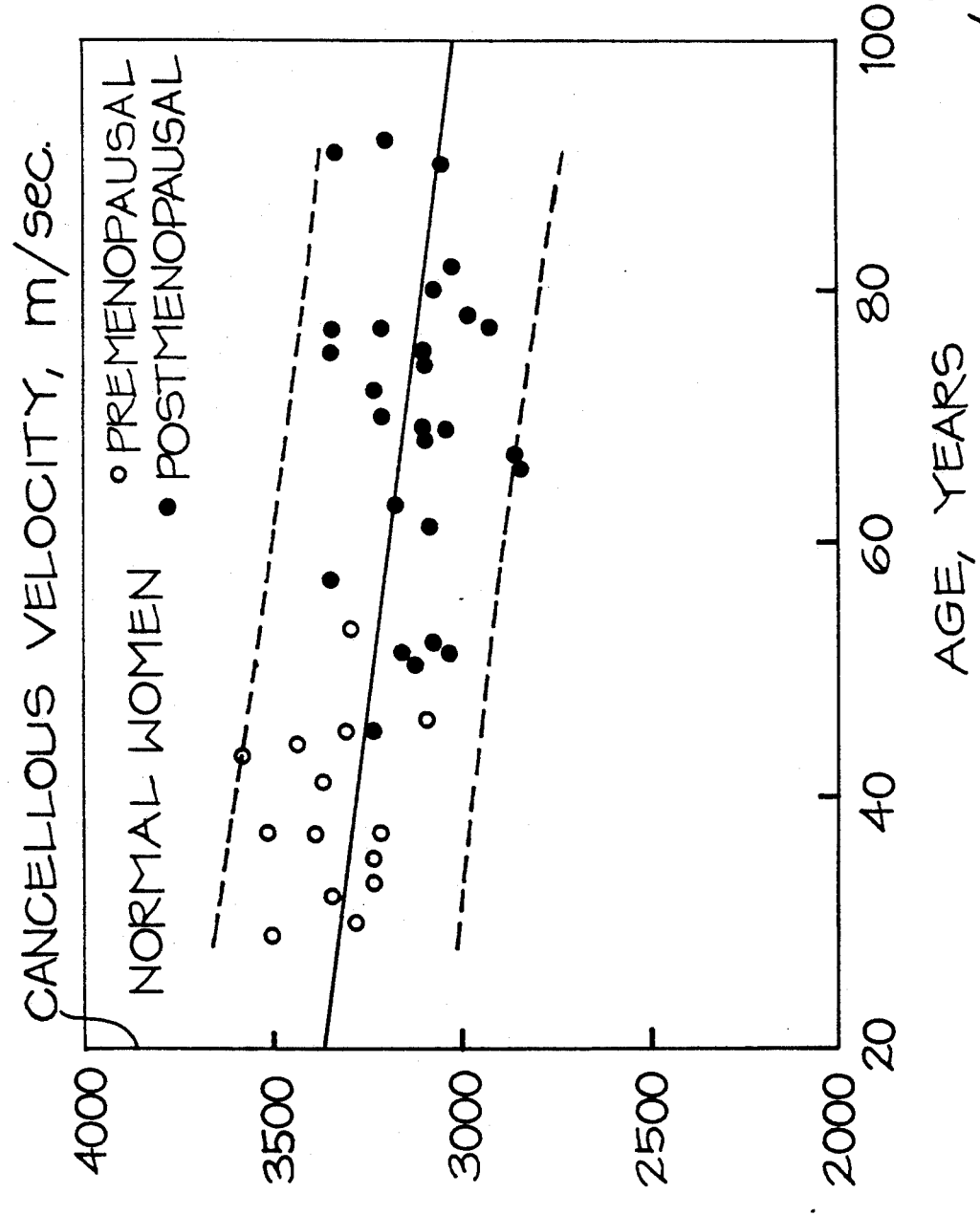
FIG. 4 shows the relationship between cancellous bone velocity and age in normal women, including 14 premenopausal women and 32 postmenopausal women. Diagonal lines indicate the regression line and the 95% confidence interval.

A "t-score" was computed to account for the age dependence of the cancellous bone velocity (Neter et al., Applied Linear Statistical Models, Second Ed., Homewood, IL: Irwin, pp. 79-80 (1985)). This score permits the direct comparison of the distribution of cancellous bone velocities observed in a given group of patients with that of normal subjects of the same age. Thus, the mean t-score for normal subjects is zero. The t-score was calculated from the relationship:

$$\text{t-score} = (V_{obs} - V_{pred})/S(V_{obs})$$

where $V_{obs}$ is the observed cancellous bone velocity, $V_{pred}$ is the velocity expected for the subject's age based on the regression for normal women shown in FIG. 4, and $S(V_{obs})$ is the estimated standard deviation of velocity for the normal group at the corresponding age.

Results of longitudinal studies were analyzed with paired t-tests, where a Bonferroni adjusted level of significance of 0.05 was assumed. Statistical analyses were performed using BMDP and CLINFO statistical software.

Reflection Ultrasound Velocity in Cancellous Bone (Ulnar Head)

In normal the cancellous bone velocity was inversely correlated with age ($r = -0.48$, p 0.001, FIG. 4). The value in normal postmenopausal women of 3124 m/sec was significantly lower than the 3341 m/sec disclosed in normal premenopausal women ($p < 0.0001$) (Table 2). The cancellous bone velocity fell by 6.7% from 3327 m/sec at 30 years of age to 3105 m/sec at 80 years of age.

Figure 5:
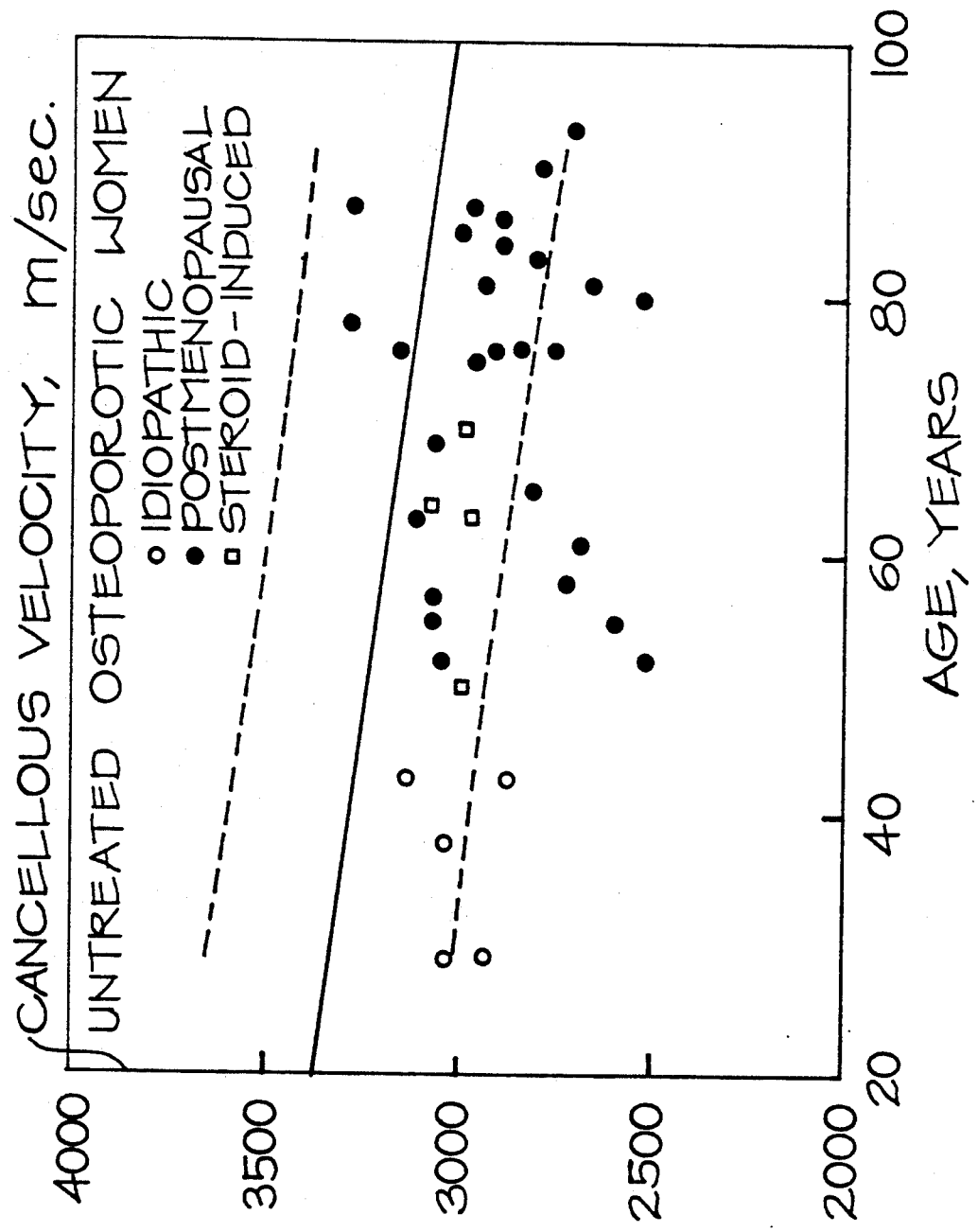
FIG. 5 shows cancellous bone velocity plotted against age in untreated osteoporotic women, including 5 with idiopathic osteoporosis, 27 with postmenopausal osteoporosis and 4 with steroid-induced osteoporosis. Diagonal lines indicate the regression line and 95% confidence interval for normal women.

In untreated patients with primary osteoporosis, the cancellous bone velocity was low (i.e. below the lower 95% confidence limit of the regression of velocity against age defined for normal subjects) in 11 of 32 patients (34.4%) (FIG. 5). It was low normal (below the regression line of normal subjects) in 18 patients (56.3%). The cancellous bone velocity was high normal (above the regression line of normal subjects) in the remaining 3 patients (9.3%). For the whole group of untreated patients with primary osteoporosis, the cancellous bone velocity was not correlated with age ($r = +0.05$, $p = 0.79$). The mean value for cancellous bone velocity in these patients of 2902 m/sec was significantly lower than the 3197 m/sec obtained in normal subjects (all normal women, $p < 0.0001$, Table 2).

TABLE 2

Reflection Ultrasound Velocity and Bone Density in Various Groups

| | N | Age yr mean | (range) | Cancellous Bone Velocity m/sec | Cortical Bone Velocity m/sec | Ulnar Head Bone Density g/cm² | Ulnar Shaft Bone Density g/cm² |
|---|---|---|---|---|---|---|---|
| Normal premenopausal | 14 | 38.7 | (29–53) | 3341 ± 136 | 4123 ± 174 | 0.327 ± 0.013 | 0.578 ± 0.034 |
| Normal postmenopausal | 32 | 69.2 | (45–92) | 3124 ± 137$^a$ | 4045 ± 199 | 0.258 ± 0.058$^h$ | 0.478 ± 0.019 |
| All normal women | 46 | 59.9 | (29–92) | 3197 ± 170 | 4071 ± 192 | 0.279 ± 0.064 | 0.508 ± 0.100 |
| Untreated osteoporosis | 32 | 69.0 | (29–93) | 2902 ± 200$^b$ | 4089 ± 178 | 0.237 ± 0.048$^d$ | 0.431 ± 0.089 |
| Treated osteoporosis, remission | 33 | 66.0 | (43–81) | 3082 ± 166$^{d,e}$ | 4160 ± 227$^g$ | 0.243 ± 0.034 | 0.427 ± 0.070 |
| Treated osteoporosis, relapse | 5 | 76.4 | (63–86) | 2911 ± 161$^f$ | 4041 ± 218 | 0.223 ± 0.034 | 0.378 ± 0.052 |
| Steroid-induced osteoporosis | 4 | 61.8 | (50–70) | 3004 ± 47$^c$ | 4015 ± 263 | 0.244 ± 0.022 | 0.421 ± 0.039 |

Values are presented as mean ± SD.
$^a$p < 0.0001 vs normal premenopausal
$^b$p < 0.0001 vs all normal women
$^c$p = 0.09 vs normal postmenopausal
$^d$p = 0.0001 vs normal premenopausal
$^e$p = 0.0002 vs untreated osteoporosis
$^f$p = 0.004 vs normal postmenopausal
$^g$p = 0.05 vs normal postmenopausal
$^h$p = 0.0005 vs normal premenopausal The cancellous bone velocity in patients with steroid-induced osteoporosis was low normal (FIG. 5). The mean cancellous bone velocity of 3004 m/sec was less than that of normal postmenopausal women of 3124 m/sec; however, the change was not significant (p=0.09).

Figure 6:
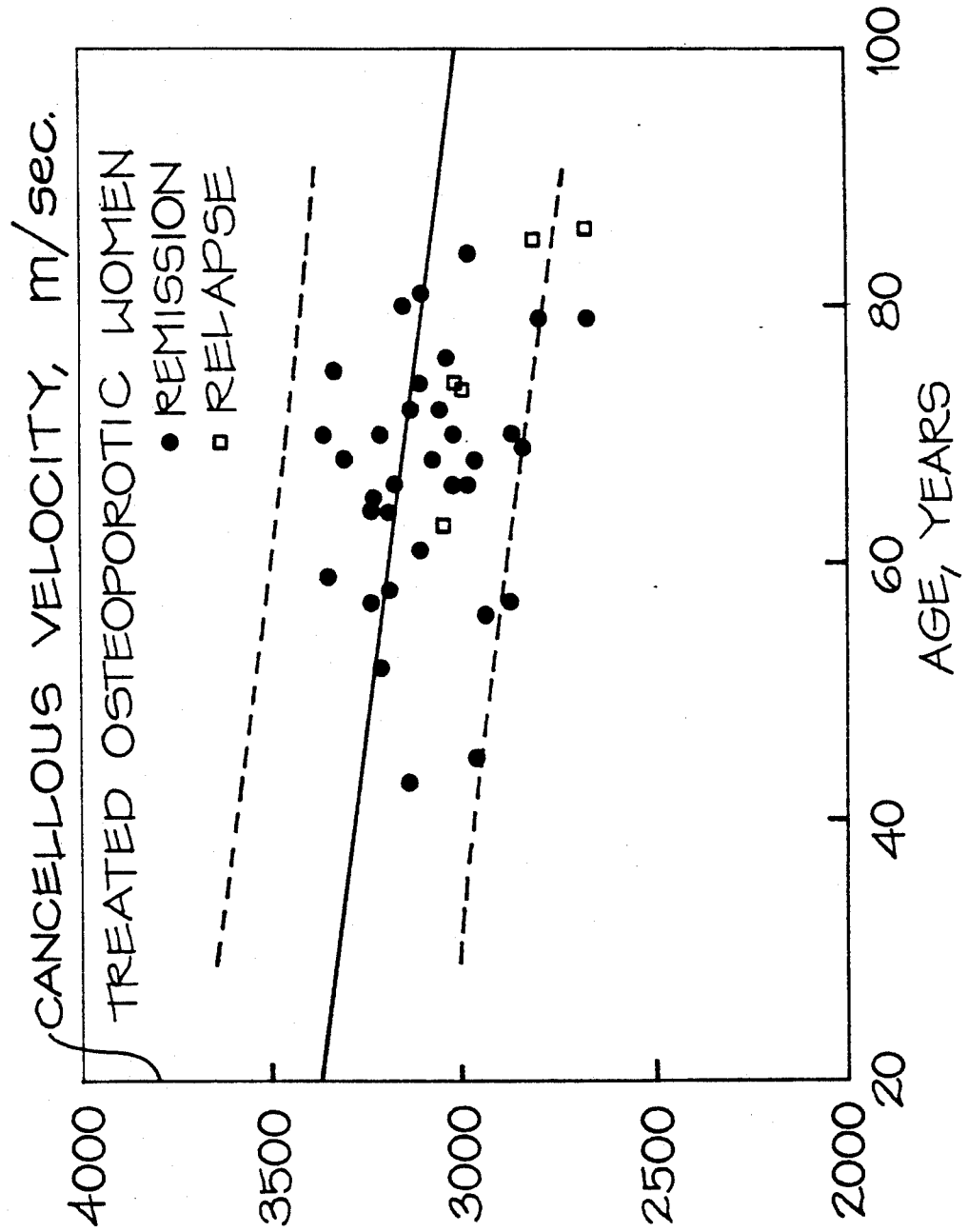
FIG. 6 shows cancellous bone velocity plotted against age in osteoporotic women treated with slow-release sodium fluoride plus calcium citrate. Those without recurrent spinal fractures (33) are in remission, while those with recurrent spinal fractures (5) are in relapse. Diagonal lines represent the regression line and 95% confidence interval defined for normal women.

Following treatment with slow-release sodium fluoride plus calcium citrate (in remission group), the cancellous bone velocity was normal (within 95% confidence interval of normal subjects) in 31 of 33 patients (94%) (FIG. 6). It was low (below the lower 95% confidence limit) in 2 patients (6%) who had been treated for only 1 year. The mean value of ultrasound velocity in treated patients in remission of 3082 m/sec was not significantly different from that of normal postmenopausal women of 3124 m/sec (p=0.28), but was lower than that of normal premenopausal women of 3341 m/sec (p=0.0001) (Table 2). The mean age of treated osteoporotic patients in remission was comparable to that of normal postmenopausal women, but higher than that of normal premenopausal women (Table 2). The velocity in treated patients in remission was significantly higher than in untreated women (p=0.0002).

In 5 treated patients with recurrent fractures, the cancellous bone velocity was low normal or low (FIG. 6). The mean value in treated osteoporotic patients in relapse of 2911 m/sec was significantly lower than 3124 m/sec found in normal postmenopausal women (p=0.004) (Table 2).

Figure 7:
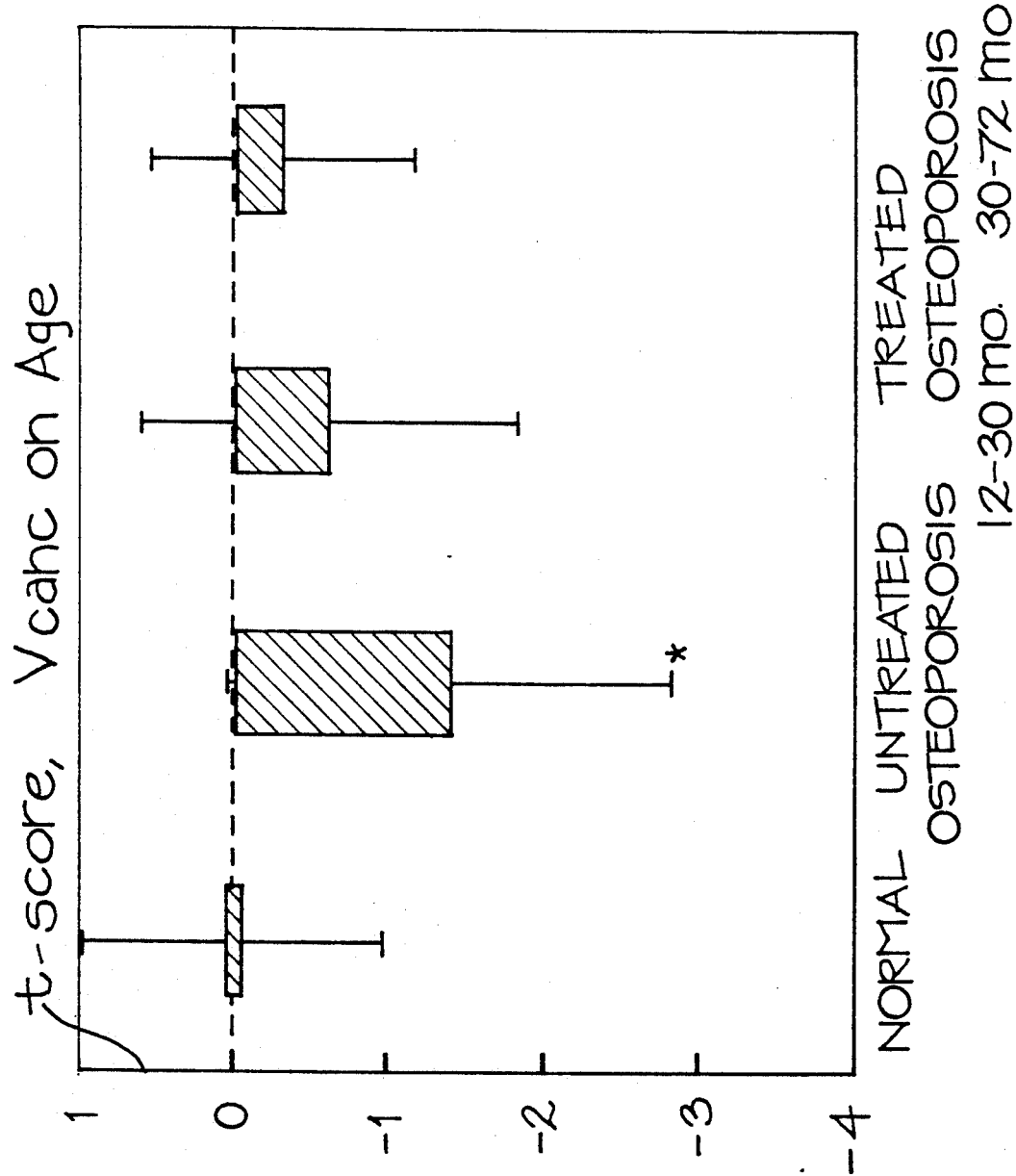
FIG. 7 shows the t-score, representing deviation from the normal mean of cancellous bone velocity on initial measurement in 4 groups of patients. Blocks represent mean values, and bars indicate standard deviations ($p < 0.0001$) from normal group.

In untreated osteoporotic patients, the t-score was −1.433, which was significantly different from zero for normal women (p<0.0001, FIG. 7). The t-score progressively declined with duration of treatment, with values in treated groups being not significantly different from that of normal women.

Longitudinal Study of Cancellous Bone Velocity in Osteoporotic Patients

In nine untreated subjects, the cancellous reflection ultrasound velocity fell from 3051 to 2977 m/sec over 8.8 months; the change was not significant (p=0.22). In nine patients treated for a short-term (12–30 months at first measurement), the cancellous velocity increased from 3037 to 3167 m/sec on repeat measurement (p=0.017). In 11 patients treated long-term (for 30–72 months at first measurement), the repeat measurement of cancellous velocity showed only a minor change from 3103 to 3141 m/sec (p=0.63).

The t-score distribution displayed the same trends. The t-score rose significantly from −0.809 to +0.058 in the "short-term" treated group (p<0.016). In untreated patients and the "long-term" treated group, there was no significant change in the t-score.

Reflection Ultrasound Velocity in Cortical Bone (Ulnar Shaft)

The cortical bone velocity was not correlated with age in normal women or in any of the patient groups. The mean value for cortical bone velocity was lower in normal postmenopausal women than in normal premenopausal women, but the change was not significant (from 4045 m/sec to 4123 m/sec, p=0.22) (Table 2). The value in untreated osteoporotic women of 4089 m/sec was not much different from that of normal postmenopausal women. The mean cortical bone velocity of 4160 m/sec in treated osteoporotic women in remission was higher than that of normal postmenopausal women (4045 m/sec, p=0.05) and that of untreated osteoporotic patients (4089 m/sec), though not significantly so (p=0.20). The values in treated osteoporotic patients in relapse of 4041 m/sec and in steroid-induced osteoporosis of 4015 m/sec were not substantially different from that of normal postmenopausal women of 4045 m/sec or of untreated osteoporotic patients of 4089 m/sec.

Bone Density and Correlation with Reflection Ultrasound Velocity

The ulnar head bone density was significantly lower in normal postmenopausal women than in premenopausal women (0.258 g/cm³ vs 0.327 g/cm³, p=0.0005). It decreased further in untreated osteoporotic women from normal premenopausal women (p=0.0001), but the change from the normal postmenopausal women was not significant (0.237 g/cm³ vs 0.258 g/cm³, P=0.13). Moreover, the ulnar head bone density in treated osteoporotic patients in remission was not significantly different from that of untreated osteoporotic patients (p=0.55). No correlation was found between cortical bone velocity and ulnar shaft bone density in normal women (r=0.20, p=0.23). In untreated osteoporotic patients, no correlation could be shown between cancellous bone velocity and ulnar head bone density (r=0.11, p=0.585), and between cortical bone velocity and ulnar shaft bone density (r=0.22, p=0.25).

Figure 8:
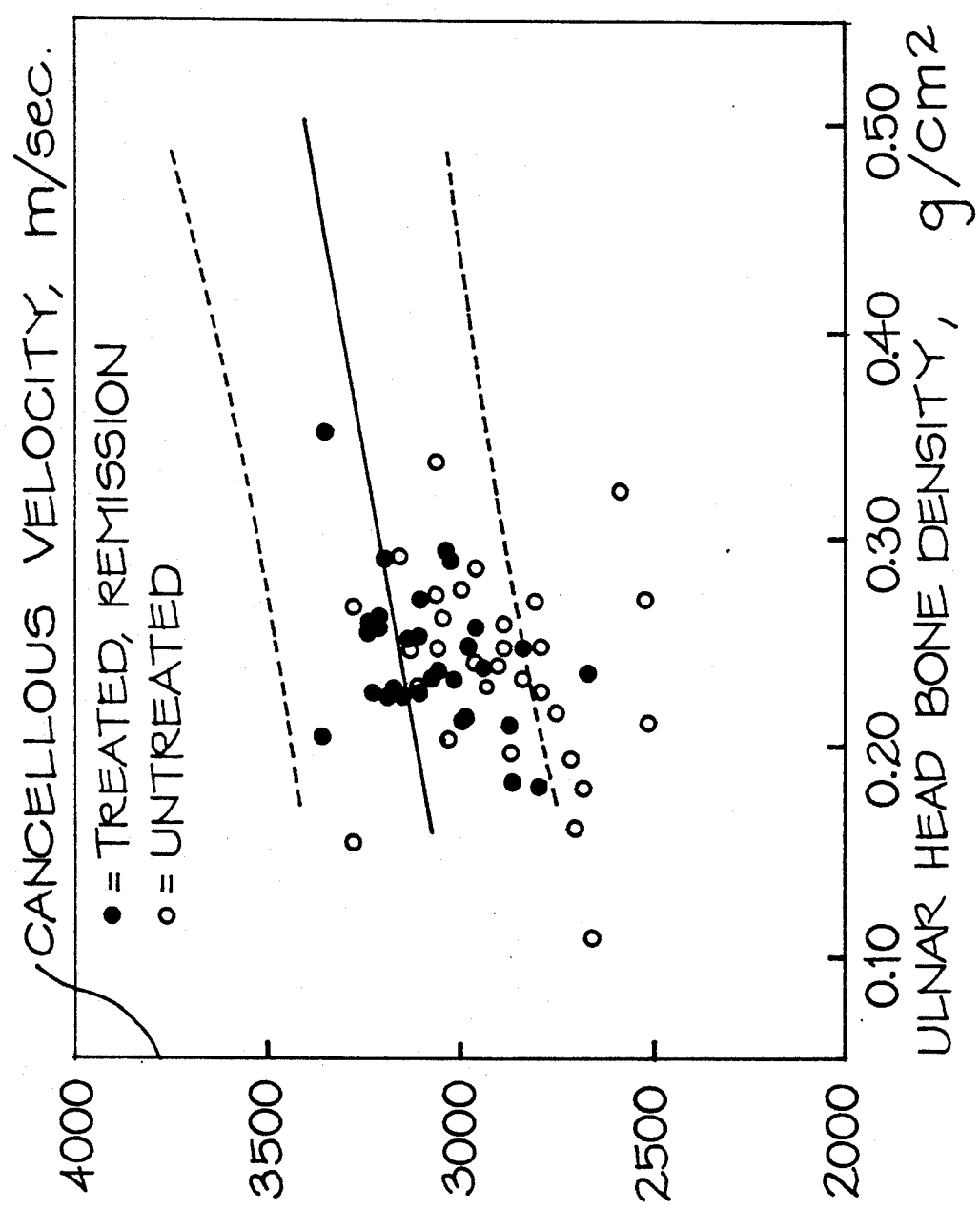
FIG. 8 shows cancellous bone velocity plotted against ulnar head bone density. Diagonal lines indicate the regression line and 95% confidence interval for normal women rather than osteoporotic patients; they are provided solely to visualize differences between reported and normal values.

In normal women, the cancellous bone velocity was weakly correlated with ulnar head bone density (r=0.39, p=0.015). In untreated patients with primary osteoporosis, the cancellous bone velocity plotted against ulnar head bone density was below the 95% confidence interval of the regression line defined for normal women in all but 2 patients (FIG. 8). Following treatment with slow-release sodium fluoride plus calcium citrate, all but one patient in remission had values which were within the 95% confidence interval of normal women.

The traditional ultrasound method for assessing bone velocity is based on detection of transmitted ultrasound (Ashman et al., J. Biomech., 17:349-61 (1984); Heaney et al., J. Am. Med. Assoc., 261:2986-90 (1989)). in vivo, however, this method does not distinguish between cortical and trabecular components in a given bone tissue, and can only be applied to a limited number of sites where bone thickness can be measured by non-ultrasound means.

The reflection ultrasound method potentially overcomes the limitations of transmission ultrasound in measuring the intrinsic quality of bone in vivo. The technique has recently been described in some detail (Antich et al., J. Bone Min. Res., 6:417-26 (1991); U.S. Pat. No. 5,038,787). Briefly, reflection ultrasound measures the velocity from the angle at which the amplitude reflected from the bone surface is maximum (critical angle). In the analysis of bone biopsies, the critical angle velocity, measured at a resolution of better than 200 microns, gave a measure of the intrinsic (material) property of cancellous bone (Zerwekh et al., J. Bone Min. Res., 6:239-44 (1991)). By positioning the center point of the sensor head first on the soft tissue-cortical bone interface, and then on the cortical bone-cancellous bone interface, the cancellous bone velocity can be measured separately from the cortical bone velocity.

Considerable experience with reflection ultrasound has already been obtained in vitro, suggesting that the velocity obtained by this approach gives useful information regarding bone quality. Reflection ultrasound velocity provides a good estimate of the transmission velocity measured at high frequency (Antich et al., J. Bone Min. Res., 6:417-26 (1991)). Ultrasound elasticity derived from transmission velocity has, in turn, been shown to be strongly correlated with the mechanical modulus of elasticity in tension and in compression for various non-biologic materials as well as cortical bone, (Ashman et al., J. Biomech., 17:349-61 (1984)) cancellous bone, (Ashman et al., J. Biomech, 20:979-86 (1987)) and individual trabeculae (Rho and Ashman, The First World Congress of Biomechanics, San Diego, Calif., p. 132 (1990)). Furthermore, elasticity correlates with strength, measured as the breaking strength in compression (Ashman et al., J. Biomech., 17:349-61 (1984)).

Young's modulus of elasticity as determined from reflection ultrasound velocities and directly measured bone density is strongly correlated with the mechanically derived modulus of elasticity (r=+0.84, p=0.0001) and breaking strength (r=0.71, p=0.0001) under tension and compression in cancellous bone specimens. The reflection ultrasound technique may also disclose brittleness of bone, since fluorotic bone has been shown to have reduced velocity in the setting of increased density (Antich et al., forthcoming). Such measurements have heretofore been made in vitro, but the present invention relates to in vivo determinations.

The ulna is chosen for in vivo measurements because of easy access and the facility with which ultrasound velocity in cancellous bone can be measured separately from the velocity in cortical bone.

In cancellous bone, the reflection ultrasound velocity in normal women is inversely correlated with age, with the value in postmenopausal women being significantly lower than in premenopausal women. Compared to age-matched values in normal women, the cancellous bone velocity is reduced in untreated patients with osteoporosis (postmenopausal, idiopathic, steroid-induced). Following treatment with slow-release sodium fluoride plus calcium citrate (Pak et al., J. Clin. Endocrin. Metab., 68:150-9 (1989); Pak et al., J. Bone Min. Res., 5:S149-55 (1990)), patients in remission (having no further spinal fractures) had a reflection ultrasound velocity which was indistinguishable from that of normal women of corresponding age. Moreover, the reflection ultrasound velocity at corresponding level of bone density was within the range of normal women in treated patients in remission, though low or low normal in untreated patients. In contrast, osteoporotic patients who continued to have spinal fractures during treatment had a cancellous bone velocity which was low normal or low compared to values in normal women. On repeat measurements in available patients approximately 9 months later, the cancellous velocity rose significantly in patients treated short-term (12-30 months), but displayed no significant change in untreated patients and those treated long-term.

The t-score, which expresses deviation from normal mean of cancellous velocity on age, showed similar changes. It was significantly lower than normal (−1.433) in untreated osteoporotic patients, but not different from normal in treated groups. Repeat measurement about 9 months later showed a significant increase in t-score to a normal value in patients treated short-term (12-30 months at first measurement), but no significant change in untreated patients and in those treated long-term.

Changes in cortical bone were comparable to those observed in cancellous bone. There was no evidence that treatment with slow-release sodium fluoride plus calcium citrate caused a reduction of cortical bone ultrasound velocity. The results indicate that the material quality of cancellous bone (and to a lesser extent of cortical bone) worsens with normal aging, that it may be further reduced in patients with spinal osteoporosis, and that this reduced strength in osteoporotic patients may be corrected by treatment with slow-release sodium fluoride and calcium citrate. Much of this correction develops independently of change in bone mass and occurs during the first 30-40 months of treatment.

The effect of treatment with slow-release sodium fluoride plus calcium citrate disclosed here contrasts with the prior understanding of fluoride action. It has been suggested that fluoride therapy may improve compressive strength of vertebra by increasing bone mass and structural strength, but that it would weaken tensile strength, especially of cortical bone, by impairing material strength. Moreover, fluorotic bone is believed to be brittle. Thus, Riggs et al. reported recently (Riggs et al., N. Eng. J. Med., 322:1265-71 (1990)) that continuous treatment with plain sodium fluoride (75 mg/day) and calcium carbonate caused a substantial rise in vertebral bone mass (35%) in 4 years. The decline in spinal fracture rate, however, was not significant, and the appendicular fracture rate actually increased.

In contrast, clinically favorable results are obtained if fluoride is given as slow-release sodium fluoride (Pak et al., J. Clin. Endocrin. Metab., 68:150-9 (1989); Pak et al., J. Bone Min. Res., 5:S149-55 (1990)) at a lower dose (25 mg twice/day) and in an intermittent format (12-month treatment periods, separated by 1 to 2 months of withdrawal). Continuous calcium supplementation with a more bioavailable calcium (calcium citrate) appears helpful (Harvey et al., J. Bone Min. Res., 3:253-8 (1988); Harvey et al., J. Am. Coll. Nutr., 9:538-87 (1990). Serum fluoride concentrations can be kept within 5-10 mmol/liter (believed to be the therapeutic window) with a circadian fluctuation of about 2.5 mmol/liter (Pak et al., J. Bone Min. Res., 5:857-62 (1990)), avoiding the wide swings in serum fluoride levels that occur with rapid-release sodium fluoride (Sakhaee et al., Bone Min., 14:131-36 (1991)).

Bone biopsies following this treatment reveal normal lamellar bone by histomorphometry (Pak et al., J. Clin. Endocrin. Metab., 68:159-9 (1989)) and normally mineralized tissue by backscattered electron image microscopy (Zerwekh et al., J. Bone Min. Res., 5(2):S181 (1990); Holmes et al., J. Biomedical Materials Res., 21:731-39 (1987)). In 81% of patients, cancellous bone reflection ultrasound velocity in bone biopsy specimens increased significantly following treatment with slow-release sodium fluoride plus calcium citrate (Zerwekh et al., J. Bone Min. Res., 6:239-44 (1991)). Comparable measurements in fluorotic bone show decreased ultrasound reflection velocity (Antich et al., forthcoming). Thus, a decline in ultrasound reflection velocity or a failure to increase with treatment suggests the possible onset of fluorosis and the need to interrupt fluoride administration temporarily, or to decrease fluoride dosage.

In summary, reflection ultrasound analysis appears to have diagnostic value because it discloses impaired cancellous bone quality (reduced reflection ultrasound velocity) due to either normal aging or osteoporosis. Further, it may be useful in assessing response to treatment of osteoporosis, since the indication of altered bone quality (low reflection velocity) in osteoporotic individuals can be corrected with appropriate therapy (such as slow release sodium fluoride).

EXAMPLE 5

The Relationship of Spinal Fracture to Bone Density in Patients Treated with Slow-Release Sodium Fluoride and Calcium Citrate The relationship between spinal fracture incidence and lumbar bone density was determined in untreated osteoporotic patients to aid interpretation of the response to treatment with slow-release sodium fluoride plus calcium citrate. In 124 untreated women with postmenopausal or estrogen-lack osteoporosis, the total number of vertebral fractures was measured individually and plotted against the corresponding L2-L4 vertebral bone density.

Between bone densities of 0.5 and 1.2 g/cm$^3$, fracture number values showed a wide scatter; the median value for each 0.1 g/cm$^3$ bone density interval did not differ significantly.

Additionally, the number of spinal fractures in sixty-two treated patients with postmenopausal or estrogen-lack osteoporosis was compared with that in untreated patients. Treated patients received slow-release sodium fluoride (25 mg twice/day) plus calcium citrate; treatment duration was 2-8 years (mean 3.8 years).

Twenty-four of sixty-two patients continued to suffer from spinal fractures. For seven of the twenty-four, the recurrent fracture number was within the 25-75th percentile of values in an untreated population; for the remaining seventeen, it was below the 25th percentile. The other 38 patients were fracture-free, even though 33 of them had final L2-L4 bone density of less than 1.0 g/cm$^3$. For the whole group of treated patients, the median spinal fracture number during treatment at each 0.1 g/cm$^3$ bone density interval was significantly lower than the median fracture number of untreated patients at the same level of bone density. Thus, slow-release sodium fluoride with calcium citrate was shown to inhibit recurrent spinal fractures by improving bone quality.

Related Studies

Recent clinical trials suggest that the relationship which has heretofore been assumed between fracture incidence and bone density is not constant. In studies of intermittent etidronate administration (Storm et al., N. Eng. J. Med., 322:1265-1271 (1990); Watts et al., N. Eng. J. Med., 323:73-79 (1990)), the spinal fracture rate significantly declined, even though the lumbar bone density rose only slightly and remained below the fracture threshold. In contrast, treatment with plain sodium fluoride at a dose of 75 mg/day with calcium carbonate (Riggs et al., N. Engl. J. Med., 322:802-809 (1990)) did not significantly alter the spinal fracture rate, even though bone density approached or even exceeded the fracture threshold. Such results suggest that another parameter (bone quality) might also affect the likelihood of fractures, and that bone formed during etidronate treatment is of superior quality to that formed with fluoride treatment (Lindsay, R., *N. Eng. J. Med.*, 322:845-846 (1990)). But another possible explanation for the differences would relate clinical effects to the method of drug administration.

For example, recent work has suggested that fluoride might improve the quality of skeletal bone if it is delivered as intermittent slow-release sodium fluoride at a dose of 50 mg/kay with continuous calcium citrate supplementation (Pak et al., J. Clin. Endocrin. Metabl. 68:150-159 (1989); Pak et al., J. Bone Min. Res., 5:S149-S155 (1990)). Bone biopsy specimens obtained after two years of this treatment were normally mineralized (Pak et al., J. Clin. Endocrin. Metabl., 68:150-159 (1989)). Further, examination of the specimens by reflection ultrasound (Antich et al., J. Bone Min. Res., 6:417-426 (1991)) showed 81% with increased critical angle velocity following treatment (Zerwekh et al., J. Bone Min. Res., 6:239-244 (1991)). The increase in critical angle velocity indicates that this treatment improves the material strength or quality of bone without concomitant changes in bone density.

To affirm this relationship, the relationship between spinal fracture number and bone density was obtained in 124 untreated patients with primary osteoporosis. These data were compared with the responses of 62 patients being treated for primary osteoporosis with slow-release sodium fluoride and calcium citrate (Pak et al., J. Clin. Endocrin. Metabl., 68:150-159 (1989); Pak et al., J. Bone Min. Res., 5:S149-S155 (1990)).

Material and Methods

To construct the relationship between spinal fracture occurrence and lumbar bone density, 124 untreated white women with primary osteoporosis were studies. All patients satisfied the following entry and exclusion criteria. They had documented "spontaneous" fracture(s) of the spine but did not have end-stage renal disease, primary hyperparathyroidism, Paget's disease of bone, osteogenesis imperfects, skeletal developmental abnormalities, osteomalacia, biliary cirrhosis, osteosclerosis, multiple myeloma, thyrotoxicosis, hyperadrenocorticosteroidism, intestinal fat malabsorption, or chronic diarrheal syndrome. None had prior therapy with fluoride, corticosteroids, calcitonin or diphosphonate, and none had taken exogenous estrogen during the preceding 4 years or for more than 2 years postmenopausally. Also excluded were patients with aortic calcification or marked scoliosis which could give an erroneously high spinal bone density.

The clinical diagnosis was postmenopausal osteoporosis in 118 patients, and 6 patients had surgical oophorectomy at an early age. The median age was 68.0 years (mean 67.4 years, range 36-87 years). The median interval from the first known spinal fracture to the time of evaluation was 3.0 years (mean 4.8 years), with a range of 0.5-23 years (Table 3).

To make the period of observation in untreated patients comparable to that in treated patients, those with intervals of 2-8 years from the first spinal fracture to the time of evaluation were selected from the total group of 124 patients. The resulting subgroup of 62 untreated patients was similar in age, lumbar bone density, and spinal fracture rates to the total untreated group (Table 3).

For assessing treatment response, recent data from an ongoing trial with slow-release sodium fluoride plus calcium citrate (Pak et al., J. Clin. Endocrin. Metabl., 68:150-159 (1989); Pak et al., J. Bone Min. Res., 5:S149-S155 (1990)) were used. The three groups of patients all had postmenopausal osteoporosis, or osteoporosis of estrogen-lack, with spinal fractures. None took estrogen, steroids, calcitonin, diphosphonate or orthophosphate. Entry and exclusion criteria were the same as described previously for untreated patients. They represented all patients who completed at least two years of trial with slow-release sodium fluoride in a non-randomized trial.

Group A comprised 19 women participating in a cyclical trial, consisting of slow-release sodium fluoride 25 mg twice/day plus calcium citrate 400 mg calcium twice/day for 12 months. Sodium fluoride was omitted for 1-2 months in each 13-14 month cycle (Group IV format) (Pak et al., J. Bone Min. Res., 5:S149-S155 (1990)). Seventeen had postmenopausal osteoporosis; two patients had surgical oophorectomy. Their presentations were comparable to that of untreated patients (Table 3). The age and the L2-L4 bone density at the last treatment visit were similar to those of untreated patients at initial evaluation. The total number of spinal fractures (median value) before treatment in Group A (treated) was 4.0/patient, compared to 5.0/patient for the untreated group. The median duration of treatment in Group A was 3.0 years/patient, the same as the interval between the first known fracture episode and the time of evaluation for the untreated group.

Group B consisted of 29 patients who participated in slightly different treatment formats, (Pak et al., J. Bone Min. Res., 1:563-571 (1986)) represented by:

Group I format (1,25-(OH)$_2$ vitamin D, 2 ug/day for 2 weeks; followed by slow-release sodium fluoride, 50 mg/day plus 25-OH vitamin D, 50 µg twice/week plus calcium citrate for 3 months; and concluded by 25-OH vitamin D and calcium citrate during the remaining 6 weeks of each 5 month cycle) (Pak et al., J. Clin. Endocrin. Metabl., 68:150-159 (1989)).

Group II format (same as Group I format except for omission of 1,25(OH)$_2$ vitamin D) (Pak et al., J. Clin. Endocrin. Metabl., 68:150-159 (1989)), and Group III format (1,25-(OH)$_2$ vitamin D, 0.5 µg/day plus slow-release sodium fluoride, 50 mg/day plus calcium citrate for 12 months; with omission of slow-release sodium fluoride for 1 month in each 13-month cycle) (Pak et al., J. Bone Min. Res., 5:S149-S155 (1990)).

Seven patients were maintained on Group I, II or III formats throughout. Twenty-two patients were initially enrolled in Group I, II or III formats and later switched to the Group IV format. Two patients had surgical oophorectomy, while the others had postmenopausal osteoporosis. The presentations of treated patients in Group B were similar to those of patients in Group A and the untreated group (Table 3).

Group C contained 14 women with postmenopausal osteoporosis participating in the same study format as Group A (Group IV format). Their presentations were similar to those of Group A Group B and the untreated group (Table 3).

TABLE 3

Presentation of Untreated and Treated Osteoporotic Patients

| | Untreated Patients | Treated Patients | | |
|---|---|---|---|---|
| | | Group A | Group B | Group C |
| No. Patients | 124 | 62 | 19 | 29 | 14 |
| Age, years, mean/median (range) | 67.4/68.0 (36-87) | 68.7/68.0 (49-83) | 66.2/66.0 (39-87) | 68.9/68.0 (44-85) | 68.4/66.5 (58-77) |
| L2-L4 Bone Density, g/cm$^2$ | 0.794 ± 0.147 | 0.804 ± 0.158 | 0.807 ± 0.153 | 0.838 ± 0.178 | 0.849 ± 0.158 |
| Pre-Spinal Fractures, no/pt, mean/median (range) | 4.9/5.0 (1-13) | 5.2/4.5 (1-13) | 4.9/4.0 (1-11) | 4.4/4.0 (1-11) | 4.5/4.0 (1-10) |
| Duration, years mean/median (range) | 4.8/3.0 (0.5-23) | 3.8/4.0 (2-8) | 3.1/3.0 (2-5) | 5.1/3.0 (2-8) | 2.0/2.0 (2) |

The age and L2-L4 bone density were at initial presentation for untreated patients, and at last treatment visity for treated patients. The pre-spinal fractures indicate total number of fractures which occurred before treatment institution. The duration represents the interval between the first fracture and the time of evaluation for untreated patients, and the length of therapy for treated patients. The ranges for age, number of spinal fractures and duration are given in parenthesis. Bone density is presented as mean ± SD.

Evaluation of Untreated Osteoporotic Patients

In 124 untreated patients, lateral spine films and L2-L4 bone densities were obtained at evaluation. Each x-ray was taken using the same instrument at the same focal length and position. Vertebral fractures were read according to the method of Riggs et al. (Riggs et al., N. Engl. J. Med., 322:802-809 (1990)). The landmarks on each vertebra from T4 to L5 were identified on lateral radiographs. Using such landmarks, vertebral heights (anterior, mid and posterior) were determined using an electrostatic digitizing board (Osteo Digital System, ESN Res., Inc.) with a coefficient of variation of 1.5%. Anterior wedge fracture was represented by a decrease in anterior/posterior height, biconcave fracture by a reduction in mid/posterior height, and vertebral collapse by a reduction in posterior height, compared to adjacent unaffected vertebra. A 15% or more reduction represented a fracture. All measurements were made by an experienced person unaware of the patient's study status. For corroboration, films showing fractures were reviewed by another person without knowledge of patient's identity or study status.

In each patient, the total number of spinal fractures was counted.

In addition, bone density of the L2-L4 spine was analyzed by dual-energy x-ray absorptiometry (Lunar Radiation, DPX 1.5), with a precision of 1%.

Assessment of Treatment Response

Lateral spine films were taken before the institution of treatment and at the last visit on treatment (after at least 2 years of treatment with slow-release sodium fluoride). The same instrument, focal length and position were used in repeat studies. Vertebral heights were measured with an electrostatic digitizing board as before. The number of fractures present on films taken before treatment was determined as described previously for untreated patients. Films taken before treatment were compared with those taken on the last treatment visit. The difference in the number of fractures disclosed between the two sets of films represented fractures which had occurred during treatment. A fracture was represented by a reduction in vertebral height of more than 15% occurring from the films at entry and the films at last follow-up visit. Also on the last treatment visit, the L2-L4 bone density was again obtained by dual-energy x-ray absorptiometry.

A careful history was taken at each visit (before treatment, every 3 months during fluoride treatment, and after temporary fluoride withdrawal) for gastrointestinal and musculoskeletal side effects, according to the method previously described (Pak et al., J. Clin. Endocrin. Metabl., 68:150-159 (1989)).

Statistical Analysis

In 124 untreated patients as well as in the subgroup of 62 untreated patients, the median, 25th percentile and 75th percentile fracture numbers were calculated for each 0.1 $g/cm^3$ bone density interval. The median rather than the mean was derived because the data were not normally distributed. The differences in median spinal fracture number between 0.1 $g/cm^3$ intervals were compared using the Kruskal-Wallis test (Conover, W. J., *Practical Nonparametric Statistics*, 2nd ed., New York: John Wiley & Sons, Inc. (1980)). The Wilcoxon Rank Sum test was used to compare fracture number of fluoride-treated patients to those of untreated patients for each bone density interval (Conover, W. J., *Practical Nonparametric Statistics*, 2nd ed., New York: John Wiley & Sons, Inc. (1980)). Prior to implementing parametric analysis, assumptions of normality were checked by the Anderson-Darling test where n was greater than 50; otherwise, the Wilk-Shapiro test was used (Conover, W. J., *Practical Nonparametric Statistics*, 2nd ed., New York: John Wiley & Sons, Inc. (1980); Anderson and Darling, *J. Amer. Statist. Assoc.*, 49:765-769 (1954)).

Figure 9:
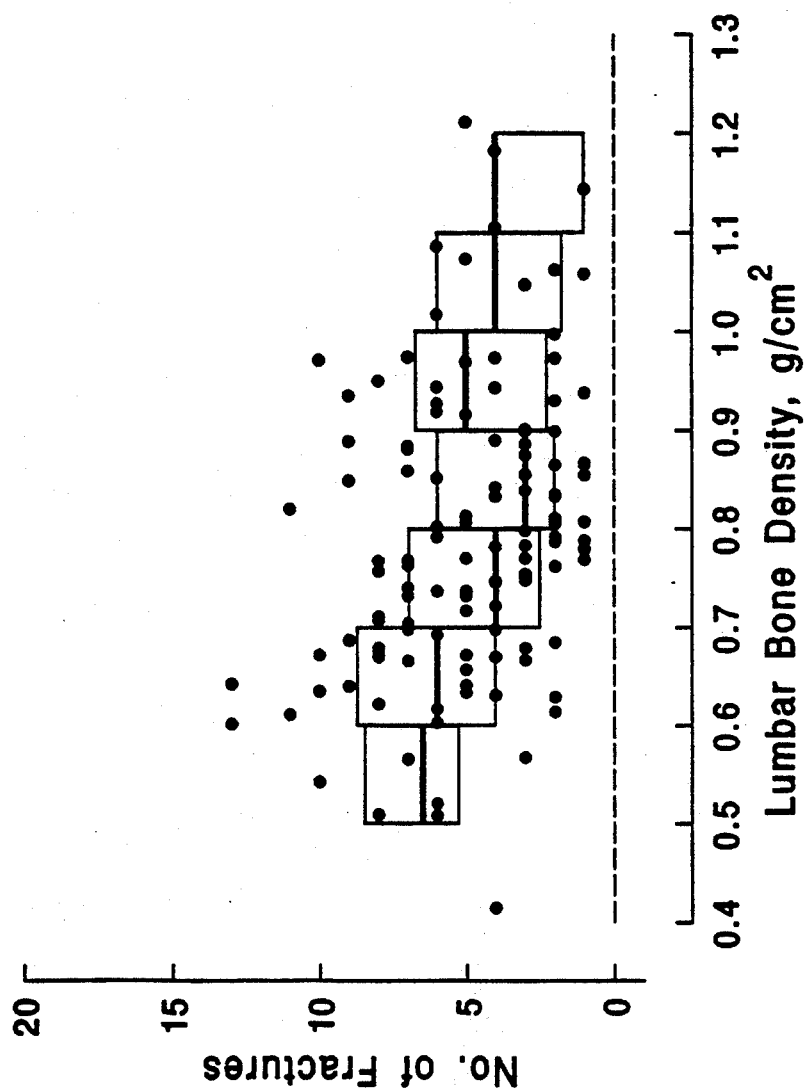
FIG. 9 shows the relationship between individual spinal fracture number and corresponding L2-L4 vertebral bone density in 124 untreated osteoporosis patients. Each point represents a study in an individual patient. Blocks indicate median, 25th percentile and 75th percentile fracture number.

Spinal Fracture Number vs Lumbar Bone Density in Untreated Osteoporosis Patients In the total group of 124 untreated patients, the L2-L4 bone density ranged from 0.42 to 1.21 $g/cm^3$ (FIG. 9). There was a wide scatter in fracture number. The median fracture number, calculated for each 0.1 $g/cm^3$ interval of bone density, tended to increase with declining bone density. However, there was no significant difference among values in the range of 0.5 to 1.2 $g/cm^3$ (where there were sufficient determinations in each 0.1 $g/cm^3$ interval to allow comparison).

Figure 10:
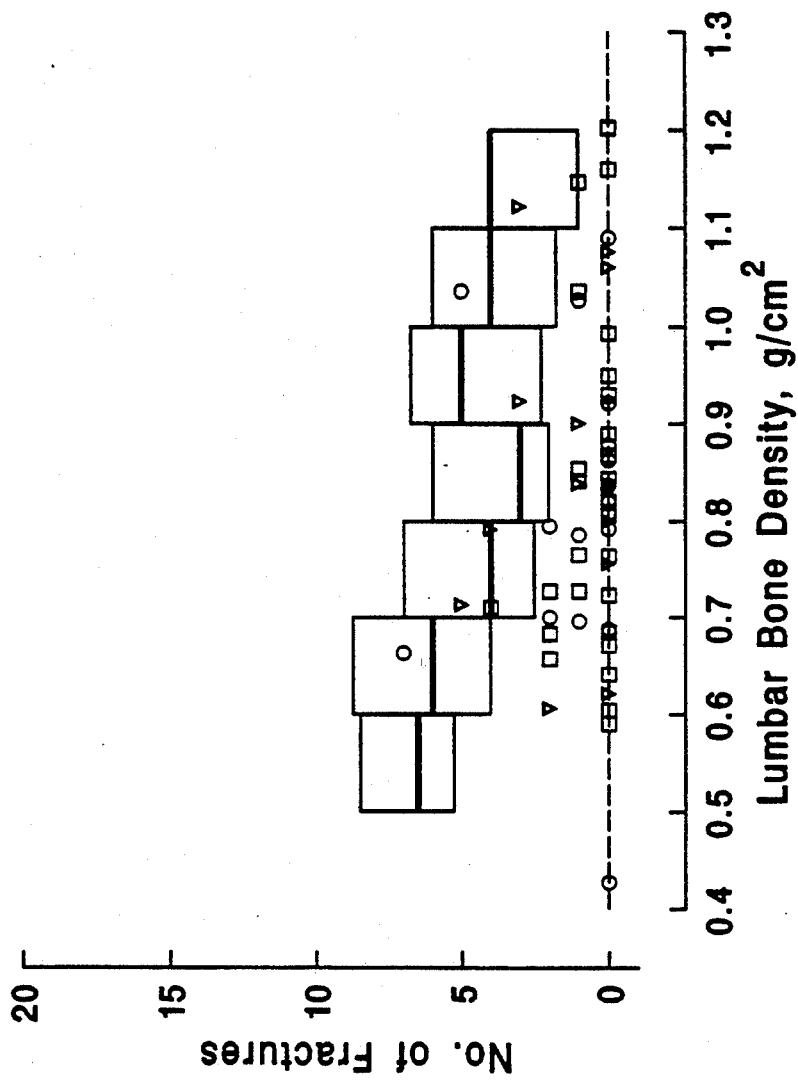
FIG. 10 shows the spinal fracture number during slow-release sodium fluoride-calcium citrate treatment in 62 patients with osteoporosis, plotted against their final L2-L4 bone density. Blocks indicate the median, 25th percentile, and 75th percentile fracture number in an untreated population of 124 (FIG. 9). Each point represents a study in an individual patient. Different symbols represent subjects from three studies.

Spinal Fracture Number Following Treatment with Slow-Release Sodium Fluoride and Calcium Citrate In FIG. 10, individual results from 62 patients receiving fluoride plus calcium treatment are plotted over the background of data from 124 untreated osteoporotic patients depicted by blocks for median, 25th and 75th percentile values for each 0.1 $g/cm^3$ bone density interval.

Of the 62 treated patients (Groups A-C), 24 patients had recurrent spinal fractures during slow-release sodium fluoride plus calcium citrate treatment, giving a relapse rate of 38.7% (FIG. 10). In 7 of the 24 patients with relapse, the number of recurrent fractures was within the 25-75th percentiles of untreated patients. In the remaining 17 patients with relapse, the recurrent fracture number was below the 25th percentile of untreated patients.

Thirty-eight of 62 treated patients did not have recurrent fractures during treatment, yielding a remission rate of 61.3% (FIG. 10). For 5 of 38 patients in remission, the L2-L4 bone density exceeded 1.0 $g/cm^3$; for the remaining 33 patients it was less.

In the bone density range 0.6-1.2 $g/cm^3$ (containing sufficient data for a meaningful statistical analysis), the median fracture rate during treatment was significantly lower than in the untreated osteoporotic population ($p<0.001$).

Figure 11:
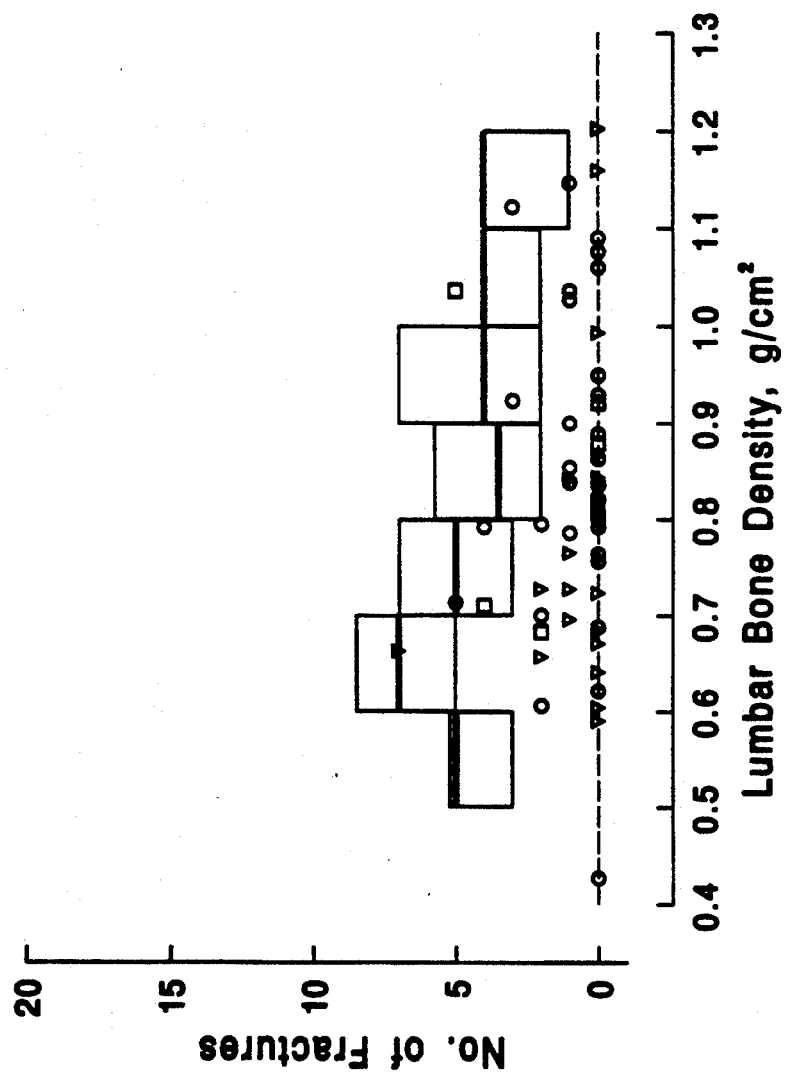
FIG. 11 shows the spinal fracture number during treatment with slow-release sodium fluoride-calcium citrate, compared with fracture number in 62 untreated patients with osteoporosis. Open circles represent patients receiving treatment for 2-3 years, open squares those treated for 3-4 years, and inverted triangles indicate patients taking treatment for 4-8 years. Blocks indicate median, 25th percentile, and 75th percentile fracture number in untreated patients, in whom the interval between the first fracture and the time of evaluation ranged from 2-8 years.

Spinal Fracture Number During Treatment: Comparison with a Comparable Untreated Group In the subgroup of 62 untreated patients (with duration from the first fracture episode to the time of evaluation ranging from 2-8 years), similar values for median, 25th percentile and 75th percentile fracture number were obtained as in the total group of 124 untreated patients (FIG. 11 vs FIG. 9). The median fracture number at varying 0.1 $g/cm^3$ bone density intervals did not differ significantly from each other.

Individual values in treated patients are shown according to varying duration of therapy in FIG. 11. There were 34 patients who received slow-release sodium fluoride plus calcium citrate for 2-3 years (greater than 2 but less than or equal to 3), 5 patients for 3-4 years, and 23 patients for 4-8 years. The three levels of treatment duration yielded values which overlapped. Among those treated for 2-3 years, 18 patients (52.9%)

were fracture-free. Similarly, in patients treated 4-8 years, 14 (60.9%) did not have recurrent fractures.

In the bone density range 0.6-1.2 g/cm$^3$, the median fracture number in treated patients was significantly lower than in the subgroup of untreated patients at the same bone density interval (p<0.001).

Other Responses to Treatment

In the combined group of treated patients (n=62), the mean duration of treatment was 3.8 years (median 3.0 years). The hip fracture rate was 21/1000 patient years. Minor gastrointestinal side effects occurred in 3.2% of patients when slow-release sodium fluoride was taken with calcium citrate or a light meal. No one had positive occult blood in feces or gastrointestinal bleeding which could be clearly attributed to treatment. No one had microfracture or lower extremity pain lasting more than 4 weeks. The L2-L4 bone density rose by 4.6%/year during treatment, but the final value was still below the "fracture threshold" of 1.1 g/cm$^2$ in most patients.

In assigning fracture risk to a given level of bone density, the total number of fractures is used, rather than fracture rate or fracture prevalence. The calculation of spinal fracture rate could be imprecise, because the exact date of the first fracture is often difficult to determine and since the initial spinal x-rays were often lacking or were taken elsewhere with a different technique. Since we considered only those patients who had spinal fractures, the fracture prevalence was already 100%.

This study disclosed a continuing rise in median spinal fracture number as the vertebral bone density decreased in untreated osteoporotic patients. However, this change was not significant, possibly due to insufficient power.

The relationship between total number of spinal fractures and vertebral bone density in untreated osteoporotic patients may be used to assess the response to treatment, if the following assumptions are made. First, residual bone mass is a major determinant of fracture. Second, the risk of fracture during treatment is the same as that of pretreatment at the same level of bone density. Third, the treated population is comparable to untreated osteoporotic patients with respect to age, severity of disease, and duration of disease or follow-up.

During treatment with slow-release sodium fluoride plus calcium citrate, a minority of patients (24 of 62) continued to have spinal fractures during treatment. In 7 of them (11.3% of total), the fracture number was appropriate for the level of bone density, since it was within the 25th-75th percentile of values in the total group of 124 untreated osteoporotic patients. Thus, the recurrent fractures could be attributed principally to a persistent low bone mass.

In the remaining 17 patients with recurrent fractures, the fracture number was below the 25th percentile of untreated patients (total group). Moreover, 38 patients were fracture-free during treatment. In these 55 patients (88.7% of total), the number of recurrent fractures was inappropriately low for the level of bone density. This finding was even more striking in 33 patients who remained fracture-free, even though their bone density remained below 1 g/cm$^3$, formerly believed to be the fracture threshold (Riggs and Melton, N. Engl. J. Med., 314:1676-1686 (1986)). Similar findings were obtained when the fracture number in treated patients was compared with the subgroup of 62 untreated patients with a comparable duration of observation (2-8 years). Thus, the majority of patients were fracture-free or had a subnormal fracture number for the level of bone density, even though the treatment duration was as long as 8 years.

The above results suggest that a change in bone quality could have modified the normal dependence of fracture propensity on bone density. They indicate that treatment with slow-release sodium fluoride and calcium citrate could have stimulated formation of mechanically improved bone, as was demonstrated in vitro (Zerwekh et al., J. Bone Min. Res., 6:239-244 (1991)) and by in vivo ultrasound analysis (Example 4).

It is difficult to ascribe the above findings entirely to the remission phase of a normal course of an osteoporotic process (Kanis, J., Lancet, i:27-33 (1984)). Many patients remained fracture-free for many years (2-8 years), even though they had severe spinal osteoporosis (shown by L2-L4 bone density of less than 1.0 g/cm$^3$ and high initial fracture count of about 4/patient) to begin with. The initial presentation of treated patients was comparable to that of untreated patients with respect to age, severity of osteoporosis and duration (Table 3).

These results are at variance with the classic concept of fluoride action. Fluoride toxicity is believed to be associated with abnormal (mosaic) bone formation, with reduced strength (Beary, D., Anat. Rec., 164:305-316 (1969); Jowsey et al., Am. J. Med., 53:43-49 (1972)). In a recent placebo-controlled randomized trial (Riggs et al., N. Engl. J. Med., 322:802-809 (1990)), Riggs et al. reported a non-significant reduction in spinal fracture rate in the fluoride-treated group, despite a rise in L2-L4 bone density by 35% to reach 1.08 g/cm$^3$. The discrepant results could be due to differences in treatment format:

1. a slow-release formulation of sodium fluoride (rather than the plain, immediate-release preparation used by Riggs et al. (Riggs et al., N. Engl. J. Med., 322:802-809 (1990)),
2. given at a lower dosage (50 mg/day instead of 75 mg/day),
3. intermittently rather than continuously,
4. with calcium citrate (instead of less bioavailable calcium carbonate (Harvey et al., J. Bone Min. Res., 3:253-258 (1988)).

The treatment described herein gave a lower peak serum fluoride level, a less marked circadian fluctuation in serum fluoride (50 ng/ml vs 200 ng/ml) and a reduced overall fluoride absorption (by less than one-half) (Pak et al., J. Bone Min. Res., 5:857-862 (1990); Sakhaee and Pak, Bone and Mineral, 14:131-136, 1991).

Determination of the relationship between spinal fracture incidence and bone density in untreated osteoporotic patients allowed a quantitative evaluation of the response to a trial with slow-release sodium fluoride plus calcium citrate treatment. This study suggests that an intermittent slow-release sodium fluoride with a continuous calcium citrate supplementation may inhibit spinal fractures, possibly by producing bone of improved quality.

EXAMPLE 6

Figure 12:
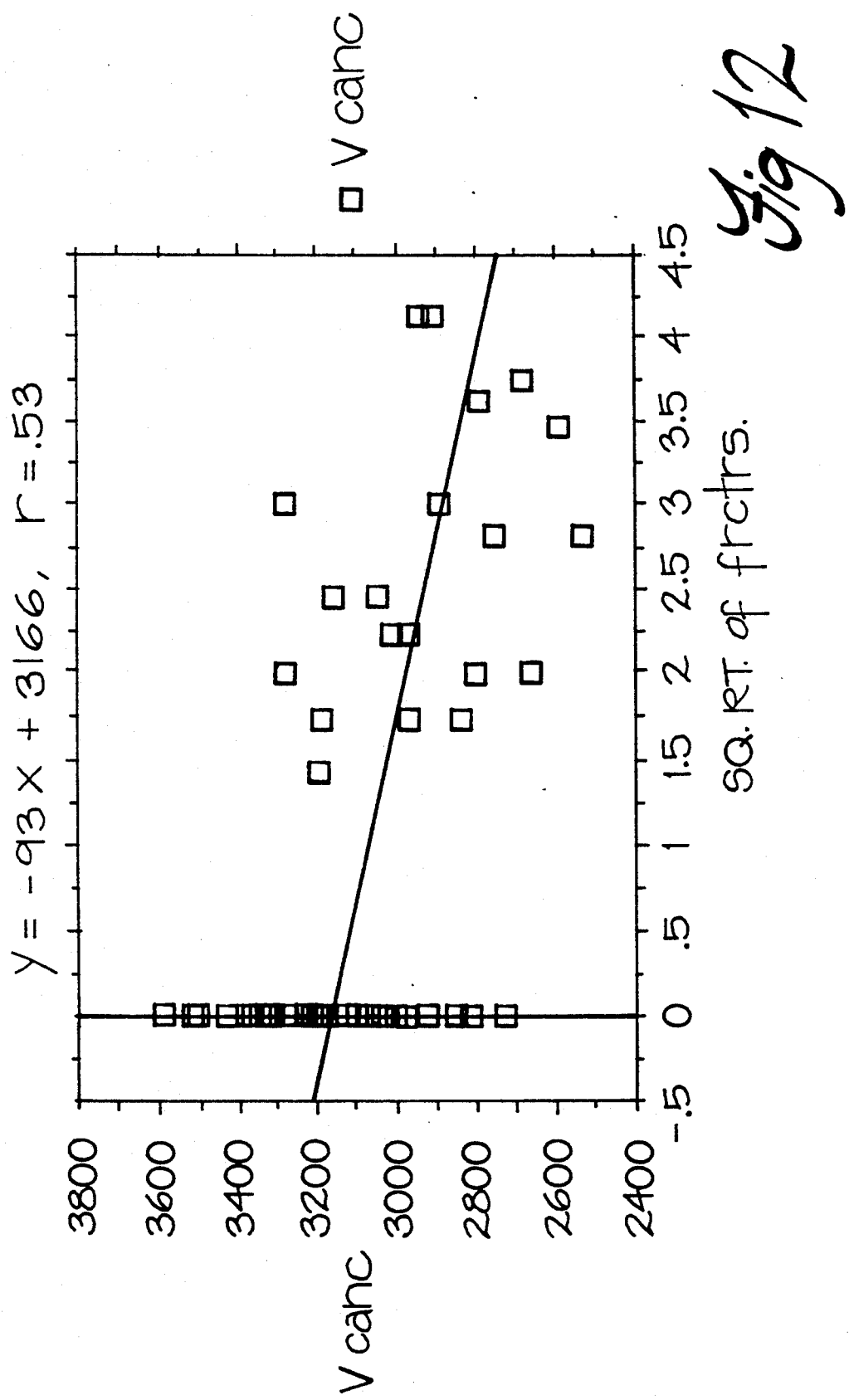
FIG. 12 shows the dependence of cancellous (ulnar bone) reflection ultrasound velocity ($V_{canc}$) on square root of vertebral fracture number.

Correlation Between Cancellous Reflection Ultrasound Velocity in Ulva and Vertebral Fracture Number In 63 untreated patients with osteoporosis, the number of vertebral fractures was determined from a lateral spine film as described above (Example 5), and the vulvar head (cancellous) reflection ultrasound velocity was measured (Example 4). The cancellous velocity ($V_{canc}$) was correlated inversely with the square of fracture number (square root of fractures) (FIG. 12). The correlation coefficient was 0.53 (p=0.0138). Thus the severity of osteoporosis varies inversely with reflection ultrasound velocity in bone.

Changes may be made in the construction, operation and arrangement of the various components, steps and procedures described herein without departing from the concept and scope of the invention as defined in the following claims.

What is claimed is:

1. A process for improving resistance to bone fracture in an osteoporotic individual, the process comprising:
   identifying an osteoporotic individual by reduced in vivo reflection ultrasound velocity in bone of the individual;
   maintaining in said osteoporotic individual a serum fluoride level between about 100 ng/ml and about 200 ng/ml with a circadian fluctuation of less than about 75 ng/ml by enterally administering slow-release sodium fluoride;
   administering enterally to said individual an amount of calcium citrate containing about 800 mg calcium per day;
   interrupting said maintaining step for a period of about 30 days to about 60 days in a 13-14 month cycle.

2. A process for improving resistance to bone fracture in an osteoporotic individual, the process comprising:
   identifying an osteoporotic individual by reduced in vivo reflection ultrasound velocity in bone of the individual;
   maintaining said individual's serum fluoride and calcium levels within therapeutic ranges by monitoring in vivo reflection ultrasound velocity in bone of the individual.

3. The process of claim 2 wherein the therapeutic range of serum fluoride levels is between about 100 ng/ml and about 200 ng/ml with a circadian fluctuation of less than about 75 ng/ml.

4. The process of claim 2 wherein the therapeutic range of serum calcium levels is between about 8.5 mg/dl and about 10.5 mg/dl.

5. The process of claim 2 wherein the reflection ultrasound velocity in bone is measured in the ulnar head and ulnar shaft.

* * * * *